US009668476B2

(12) United States Patent
Lu et al.

(10) Patent No.: US 9,668,476 B2
(45) Date of Patent: *Jun. 6, 2017

(54) REMOVABLE ANTIMICROBIAL COATING COMPOSITIONS AND METHODS OF USE

(75) Inventors: Helen S. M. Lu, Wallingford, PA (US); Christian Lenges, Wilmington, DE (US); Barry Stieglitz, Wynnewood, PA (US); Lynn Leger, Mississauga (CA); Christian Hoffman, Newark, DE (US); Judith J. Vangorp, Wilmington, DE (US); Shaun F. Malone, Ajax (CA)

(73) Assignee: LANXESS Corporation, Pittsburgh, PA (US)

( * ) Notice: Subject to any disclaimer, the term of this patent is extended or adjusted under 35 U.S.C. 154(b) by 1282 days.

This patent is subject to a terminal disclaimer.

(21) Appl. No.: 11/710,325

(22) Filed: Feb. 23, 2007

(65) Prior Publication Data

US 2007/0275101 A1 Nov. 29, 2007

Related U.S. Application Data

(60) Provisional application No. 60/776,081, filed on Feb. 23, 2006, provisional application No. 60/831,983, filed on Jul. 19, 2006.

(51) Int. Cl.
| | | |
|---|---|---|
| *A01N 33/12* | (2006.01) | |
| *A23L 3/3526* | (2006.01) | |
| *A61L 2/232* | (2006.01) | |
| *A61K 9/70* | (2006.01) | |
| *C09D 5/00* | (2006.01) | |
| *C09D 5/14* | (2006.01) | |
| *C09D 5/16* | (2006.01) | |

(52) U.S. Cl.
CPC ............ *A01N 33/12* (2013.01); *A23L 3/3526* (2013.01); *A61K 9/7015* (2013.01); *A61L 2/232* (2013.01); *C09D 5/008* (2013.01); *C09D 5/14* (2013.01); *C09D 5/1625* (2013.01); *C09D 5/1668* (2013.01); *A23V 2002/00* (2013.01)

(58) Field of Classification Search
CPC .... A01N 2300/00; A01N 33/12; A01N 59/16; A01N 25/34; A01N 37/40; A01N 25/24; A01N 37/36; A01N 47/44; A01N 31/02; A01N 37/04; A01N 55/00; A01N 25/10; A01N 35/02; A01N 37/02; A01N 47/36
See application file for complete search history.

(56) References Cited

U.S. PATENT DOCUMENTS

| | | | |
|---|---|---|---|
| 3,264,272 A | 8/1966 | Rees | |
| 3,657,175 A | 4/1972 | Zimmerman | |
| 3,993,777 A | 11/1976 | Caughman et al. | |
| 4,115,292 A * | 9/1978 | Richardson et al. | ......... 510/392 |
| 4,384,096 A | 5/1983 | Sonnabend | |
| 4,567,221 A * | 1/1986 | Maruyama et al. | .......... 524/436 |
| 4,600,761 A | 7/1986 | Ruffner et al. | |
| 4,743,698 A | 5/1988 | Ruffner et al. | |
| 4,783,340 A * | 11/1988 | McDonell et al. | ............ 427/2.1 |
| 4,792,343 A | 12/1988 | Hawe et al. | |
| RE33,156 E | 1/1990 | Shay et al. | |
| 5,017,369 A * | 5/1991 | Marhevka | ..................... 424/407 |
| 5,102,936 A | 4/1992 | Huth et al. | |
| 5,234,974 A | 8/1993 | Calhoun et al. | |
| 5,294,692 A | 3/1994 | Barron et al. | |
| 5,398,846 A | 3/1995 | Corba et al. | |
| 5,585,407 A * | 12/1996 | Patel et al. | .................. 514/772.6 |
| 5,624,634 A | 4/1997 | Brougham et al. | |
| 5,817,325 A * | 10/1998 | Sawan et al. | ................. 424/411 |
| 5,874,164 A * | 2/1999 | Caldwell | .................... 428/306.6 |
| 5,888,501 A * | 3/1999 | Backman et al. | ........... 424/93.4 |
| 5,990,233 A | 11/1999 | Barron et al. | |
| 6,025,431 A | 2/2000 | Cardinali et al. | |
| 6,136,776 A | 10/2000 | Dickler et al. | |
| 6,228,354 B1 * | 5/2001 | Jeng | .......................... 424/78.07 |
| 6,306,810 B1 | 10/2001 | Cheung et al. | |
| 6,365,169 B1 * | 4/2002 | Rosenblatt | ..................... 424/404 |
| 6,391,840 B1 | 5/2002 | Thompson et al. | |
| 6,437,009 B1 | 8/2002 | Meier et al. | |
| 6,683,036 B2 * | 1/2004 | Foley et al. | .................. 510/197 |
| 6,749,869 B1 | 6/2004 | Richter et al. | |
| 6,939,554 B2 | 9/2005 | McDonald et al. | |
| 2002/0086936 A1 | 7/2002 | Eoga | |
| 2002/0185199 A1 | 12/2002 | Myers et al. | |
| 2003/0158459 A1 | 8/2003 | Tucker | |
| 2003/0203991 A1 | 10/2003 | Schottman et al. | |
| 2004/0018787 A1 | 1/2004 | Bullock et al. | |
| 2005/0008526 A1 | 1/2005 | Bianchetti et al. | |
| 2005/0014427 A1 | 1/2005 | Yoda et al. | |

(Continued)

FOREIGN PATENT DOCUMENTS

| | | |
|---|---|---|
| DE | 29903267 A1 | 6/1999 |
| DE | 29903267 U1 | 6/1999 |

(Continued)

OTHER PUBLICATIONS

Kenawy et al., "Biologically Active Polymers, 6a, Synthesis and Antimicrobial Activity of Some Linear Copolymers with Quarternary Ammonium and Phosphonium Groups", Macromolecular Bioscience, 3(2), 2003, pp. 107-116.
PCT International Search Report and Written Opinion for International Application No. PCT/US2007/004716 dated Oct. 5, 2007.
Witucki, Gerald L., "A Silane Primer:Chemistry and applications of Alkoxy Silanes", Journal of Coatings Technology, Jul. 1993, pp. 57-60, vol. 65, No. 822, Federation of Societies for Coatings Technology, Blue Bell, PA, USA.
Krysinski et al., Effect of Cleaners and Sanitizers on Listeria Monocytogenes Attached to Product Contact Surfaces, Journal of Food Protection, Apr. 1992, pp. 246-251, vol. 55, No. 4.
Chmielewski et al., Biofilm Formation and Control in Food Processing Facilities, Comprehensive Reviews in Food Science and Food Safety, 2003, pp. 22-32, vol. 2.
Kenawy et al., Synthesis and Antimicrobial Activity of Some Linear Copolymers With Quaternary Ammonium and Phosphonium Groups, Macromol. Biosci., 2003, pp. 107-116, vol. 3.

(Continued)

*Primary Examiner* — Audrea Buckley

(57) ABSTRACT

This invention relates to a method for controlling microorganisms comprising coating a surface with a removable, antimicrobial film-forming composition.

19 Claims, 3 Drawing Sheets

(56) References Cited

U.S. PATENT DOCUMENTS

| | | |
|---|---|---|
| 2005/0064176 A1 | 3/2005 | Terry |
| 2005/0139608 A1 | 6/2005 | Muehlhausen et al. |
| 2005/0175568 A1 | 8/2005 | Asari et al. |
| 2005/0215663 A1 | 9/2005 | Berge et al. |
| 2005/0245671 A1 | 11/2005 | Moon et al. |
| 2005/0250668 A1* | 11/2005 | Serobian et al. ............. 510/466 |
| 2006/0008585 A1* | 1/2006 | Woodhall et al. ............. 427/282 |
| 2006/0039953 A1 | 2/2006 | Leung et al. |
| 2006/0165742 A1 | 7/2006 | Reizlein et al. |
| 2006/0217515 A1 | 9/2006 | Getman et al. |
| 2007/0275101 A1 | 11/2007 | Lu et al. |
| 2007/0275929 A1 | 11/2007 | Fuls et al. |
| 2008/0021113 A1 | 1/2008 | Cheung et al. |
| 2008/0026026 A1 | 1/2008 | Lu et al. |
| 2008/0138312 A1 | 6/2008 | Kritzler |

FOREIGN PATENT DOCUMENTS

| | | | |
|---|---|---|---|
| EP | 0715899 A1 | 12/1996 | |
| EP | 0807156 B1 | 3/2001 | |
| FR | 2552097 A1 | 3/1985 | |
| GB | 1553132 | 9/1979 | |
| GB | 1604562 | 12/1981 | |
| JP | 19874202 A | 1/1987 | |
| JP | 1994346029 A | 12/1994 | |
| JP | 2009102314 A | 5/2009 | |
| WO | 9703135 A1 | 1/1997 | |
| WO | WO99/60085 | * 11/1999 | ................... 424/401 |
| WO | WO9960085 A1 | 11/1999 | |
| WO | 0011713 A1 | 3/2000 | |
| WO | 0102496 A2 | 1/2001 | |
| WO | 0182694 A1 | 11/2001 | |
| WO | 02087339 A1 | 11/2002 | |
| WO | 2005123270 A2 | 12/2005 | |
| WO | 2006081617 A1 | 8/2006 | |
| WO | 2007070649 A2 | 6/2007 | |
| WO | 2007100653 A2 | 9/2007 | |
| WO | 2007100654 A2 | 9/2007 | |
| WO | 2007100861 A1 | 9/2007 | |

OTHER PUBLICATIONS

Frank et al., Surface-Adherent Growth of Listeria Monocytogenes is Associated With Increased Resistance to Surfactant Sanitizers and Heat, Journal of Food Protection, Jul. 1990, pp. 550-554, vol. 53, No. 7.

Boulange-Petermann, Processes of Bioadhesion on Stainless Steel Surfaces and Cleanability: A Review With Special Reference to the Food Industry, Biofouling, 1996, pp. 275-300, vol. 10, No. 4.

Holah et al., Cleanability in Relation to Bacterial Retention on Unused and Abraded Domestic Sink Materials, Journal of Applied Bacteriology, 1990, pp. 599-608, vol. 69.

Timperley et al., Implications of Engineering Design in Food Industry Hygiene, Biofilms—Science and Technology, 1992, pp. 379-393.

Germicidal andDetergent Sanitizing Action of Disinfectants. Official Methods of Analysis of the Assn. of Official Analytic Chemistrs, paragraph 960.09, 15th Edition, 1990 (EPA Guideline 91-2). (Book not included).

Marmion, Handbook of U.S. Colorants, Foods, Drugs, Cosmetics and Medical Devices, John Wiley & Sons, Yew York, 1991 (Book not included).

Witucki, A Silane Primer: Chemistry and Applications of Alkoxy Silanes, Journal of Coatings Technology, 65 (822) pp. 57-60, 1993.

Akzo Nobel, Technical Information, Thickening With Polymers, Jan. 2010, XP-002609717.

CIBA RHEOVIS Rheology Modifiers, Viscosity Control in H&FC Formulations With Rheovis Polymers, Oct. 2003, XP-002609722.

Co-Pending U.S. Appl. No. 11/710,290, filed Feb. 23, 2007.

Co-Pending U.S. Appl. No. 12/843,120, filed Jul. 26, 2010.

International Search Report for International Application No. PCT/US2010/043382 Dated Jul. 27, 2010.

International Search Report for International Application No. PCT/US2007/004716, Dated Oct. 5, 2007.

Meyer, Determination of Benzalkonium Chloride by Reversed-Phase High-Pressure Liquid Chromatography, Journal of Pharmaceutical Sciences, 1980, pp. 1148-1150, vol. 69.

International Search Report for International Application No. PCT/US2007/004717.

* cited by examiner

Figure 1. Mechanisms by which the coating composition provides protection.

Arrows indicate migration of biocidal active into microbially-contaminated regions above and below the antimicrobial coating. The coating composition also provides a physical barrier to soil and other solid contaminants.

Figure 2: x-z-cross-sections through polymer film formed from formulation #2 (top) and y-z-cross-sections of the same film (bottom). The film was visualized by confocal laser-scanning microscopy after addition of traces of a fluorescent dye (rhodamine 123) to the film forming composition.

Figure 3. Release QAC fraction (*i.e.* mass of QAC released per total available mass of QAC in coating) over time from films sprayed from the liquid formulas #19, #20 and #21 on stainless steel surfaces, then dried and submerged into deionized water of 20 °C.

REMOVABLE ANTIMICROBIAL COATING COMPOSITIONS AND METHODS OF USE

This application claims the benefit of U.S. Provisional Application No. 60/776,081, filed Feb. 23, 2006 and U.S. Provisional Application No. 60/831,983 filed Jul. 19, 2006, both of which are incorporated by reference herein for all purposes as if fully set forth.

FIELD OF THE INVENTION

This invention relates to a method for controlling microorganisms comprising coating a surface with a durable removable, antimicrobial film-forming composition and said compositions.

BACKGROUND

The present invention relates to a method for providing control of microorganisms at a locus by contacting said locus with a removable coating composition comprising at least one antimicrobial agent.

Microbial infection represents a serious continuing problem in human and animal health. Exposure to microbial pathogens can occur in a variety of settings, such as public facilities, hospitals, consumer products contamination, food processing plants, to name a few. Inefficient cleaning of surfaces could lead to cross contamination. Furthermore, when microbes attach to the surface, biofilm forms on the surface. Microbes within a biofilm are more resistant to disinfectants. It is thus desirable to develop an coating composition that could be applied to a variety of surfaces, and that will control the microbial contamination for a prolonged period of time. It is further desirable to have a removable coating composition that would allow for the ready removal of the said coating. The removal of the coating may be required for product quality, or in preparation for a subsequent operation such as painting, or reapplication of the antimicrobial coating composition.

The control of pathogenic microorganisms such as mold, mildew, algae, fungi and other microbes, has long been a matter of concern. Biocides such as mildewcide, antimicrobial, antiseptic, disinfectant, sanitizer, germicide, algaecide or preservatives are commonly used to remove microbes from an area and prevent their recurrence. The use of biocides in the control or prevention of microbial growth requires effective contact between the biocide and the microbe. Another requirement is for the biocide to be in contact with the microbe for the required contact time sufficient to achieve the desired level of control. Commonly encountered problems in achieving effective and long lasting control of microbial growth with current and/or commercially available biocidal compositions are: insufficient contact time caused by dripping off of the biocide solution, inefficient surface coverage by non-homogeneous coating of the surfaces, and lack of residual activity to protect the surface against fresh contamination.

Good spreading properties of the liquid antimicrobial formulation onto the surface after application is beneficial in achieving a homogeneous and continuous film, especially when spraying or aerosolizing is used as the application method. Good spreading properties can enhance the antimicrobial properties of an antimicrobial formulation by achieving complete surface coverage without leaving uncovered gaps in the created antimicrobial film in which microorganisms would still be able to grow. Antimicrobial properties can further be enhanced by reducing surface tension which allows liquid antimicrobial formulations to flow into imperfections that might exist on the surface and which may harbor microorganisms.

U.S. Pat. No. 5,585,407 provides water-based coating compositions that can be applied to a substrate to inhibit growth of microbes for extended periods of time. The coating comprises an acrylate emulsion polymer and an organoalkoxysilane and can be removed under alkaline conditions.

U.S. Pat. No. 5,017,369 provides a prophylactic treatment of mastitis in a cow between milkings comprising coating the cow teats with an aqueous composition comprising an antimicrobial agent. The composition comprises at least 2 wt % partially hydrolyzed polyvinyl alcohol, from about 0 wt % to about 10 wt % of an opacifier, about 0.1 wt % to about 10 wt % of an antimicrobial agent, and at least 65 wt % water. A water wash is used to remove the film from the cow teat prior to milking.

Thus, a need exists for a disinfectant composition capable of forming a film or coating on surfaces, including hard-to-reach surfaces, and other surfaces, such as hard surfaces formed of ceramics, glass, formica, plastics, metals and the like, which film can entrain germicidal substances such as a quaternary ammonium compound or a phenolic compound. A further need exists for a disinfectant film or coating providing extended protection against microbial contamination. Additionally a need exists for easily removable long-lasting, homogeneous and continuous films or coatings that can be applied on a variety of surfaces. None of the above methods and coatings applied in said methods provide for a durable and yet readily removable coating composition for coating surfaces described herein. Thus, the problem to be solved is the lack of a method for controlling microorganisms at a particular locus with a coating composition, comprising at least one antimicrobial agent, wherein said coating is durable, provides residual antimicrobial efficacy and is readily removable.

SUMMARY

The present invention addresses problems identified above with the following methods and compositions, and in particular, a method for controlling microorganisms at a particular locus with a coating composition, comprising at least one antimicrobial agent, wherein said coating is durable, provides residual antimicrobial efficacy and is readily removable, is provided.

An aspect of the invention is directed to a method of providing control of microorganisms at a locus comprising
  a) providing a removable liquid coating composition comprising:
    i) a film-forming water soluble or water-dispersible agent;
    ii) at least one antimicrobial agent;
    iii) an inert solvent; and
    iv) a surfactant that lowers the surface tension of the formulation below 40 mN/m; and
  b) applying said composition to the locus.

In another aspect, the surfactant is a nonionic organosilicone.

In another aspect, an antifoaming agent is added to the liquid coating composition before the composition is applied to a locus.

In another aspect, the liquid coating composition is applied to a locus as a foam, whereby the composition serves as a temporary visual indicator that the surface has been covered by application of the composition on said locus. In a further aspect, an antifoaming agent is added and serves as an indicator that a film or coating has been formed after application and drying on said locus. Upon drying, the antifoaming agent results in removal of gas bubbles, which when not visible indicate that the composition is dry.

In another aspect, the liquid coating composition also contains at least one rheology agent that provides shear-thinning properties to the coating composition. In a further aspect, said shear thinning properties comprise a ratio of the viscosity at a shear rate of 5 s$^{-1}$ and the viscosity at a shear rate of 190 s$^{-1}$ is between 1.5 and 50.

In another aspect, the coating is removed with an aqueous solution at a temperature of about 15° C. to about 100° C., or more preferably at a temperature of about 30° C. to about 80° C.

In one aspect of the invention the film-forming agent is one or more of the following polymers, polyvinyl alcohols, polyvinyl alcohol copolymers, polyvinyl pyrrolidones, acrylate copolymers, ionic hydrocarbon copolymers, and polyurethanes.

In another aspect of the invention the coating composition further comprises one or more plasticizer, surfactant, cross-linking agent, colorant, solubilizing agent, rheology modifier, antioxidant, pH adjuster, wefting agent, antifoaming agent, extender, lubricant, processing aid, color fastness agent, performance enhancing agent or enzyme.

In another aspect of the invention the antimicrobial agent is one or more antimicrobials, mildewcides, antiseptics, disinfectants, sanitizers, germicides, algicides, antifouling agents or mixtures thereof, such as a quaternary ammonium compound or mixtures thereof.

In other aspects of the invention the locus is food processing equipment or other surfaces such as walls, pipes or drains; animal care facility, animal care equipment or animal husbandry or hatchery facility; a surface in a hospital or other medical or veterinary or animal care facility, animal care equipment, or animal husbandry or hatchery facility; animal hides, fur, and carcasses; or a food surface, including one or more of beef, poultry, pork, vegetables, fruits, seafood, and combinations thereof.

In other aspects of the invention, the locus is a fibrous substrate, including yarns, fibers, fabrics, textiles, nonwovens, carpets, leather and paper.

Another aspect of the invention is a method of controlling microbial contamination of a surface comprising:
  a) providing a removable liquid coating composition comprising:
    i) a film-forming water soluble or water-dispersible agent;
    ii) at least one antimicrobial agent;
    iii) an inert solvent; and
    iv) a surfactant that lowers the surface tension of the formulation below 40 mN/m; and
  b) applying said composition to said surface whereby a film is formed on said surface; and
  c) optionally, removing said film with an aqueous solution at a temperature of about 15 to about 100° C.

In another aspect, control of microorganisms at said locus comprises a reduction of at least one bacterial strain of at least 3-log or at least 5-log. In another aspect control of microorganisms includes prevention of growth of at least one type of microorganism, a reduction of microorganisms wherein said microorganisms are harbored in biofilms, providing residual antimicrobial efficacy when applied to a contaminated surface, and protection as a disinfectant, sanitizer, preservative, or a physical barrier to microbial contamination.

In another aspect of the invention, the compositions described herein may be applied to a locus to control microorganisms such as bacteria, fungi, or molds in either planktonic or biofilm state; to inhibit growth of said microorganisms, to act as barrier against contamination of said microorganisms; or to trap and prevent release of said microorganisms, in one or more of the following settings or surfaces: hatchery equipment, farm facilities, drains, pipes, oil recovery equipment, garbage cans, showers and other bathroom surfaces, surgical suites, walls, toilet bowls, vacation homes, boats, sinks, counters, cutting boards, decks, siding of homes, asphalt shingles on roofs, patios, plywood, lumber, as a temporary coating for remediation, spas, wet and dry floors.

Another aspect of the invention is an antimicrobial composition comprising components described above, including in particular:
  i) a film-forming water soluble or water-dispersible agent having a concentration in the range of 1 to 30 wt % of the composition;
  ii) at least one antimicrobial agent having a concentration of at least about 0.001 wt %;
  iii) an inert solvent at a concentration of at least about 50 wt %; and
  iv) a surfactant that provides a surface tension of the composition below 40 mN/m.

In another aspect, said antimicrobial composition further comprises one or more: plasticizer, cross-linking agent, colorant, solubilizing agent, rheology modifier, antioxidant, pH adjuster, antifoaming agent, lubricant, processing aid, color fastness agent, performance enhancing agent, or enzyme.

In further aspects, said composition provides residual antimicrobial efficacy when applied to a contaminated surface, is a disinfectant, sanitizer, preservative, or a physical barrier to microbial contamination when applied to a locus.

BRIEF DESCRIPTION OF FIGURES

The invention can be more fully understood from the following Detailed Description and the accompanying Figures.

FIG. 1 shows mechanisms by which the coating composition provides protection. Arrows indicate migration of biocidal active component into microbially-contaminated regions above and below the antimicrobial coating. The coating composition also provides a physical barrier to soil and other solid contaminants.

FIG. 2 shows confocal laser-scanning microscopy of the film. Shown are x-z-cross-sections through the polymer film formed from Formulation #2 (top), and y-z-cross-sections of the same film (bottom). The film was visualized by confocal laser-scanning microscopy after addition of traces of a fluorescent dye (rhodamine 123) to the film-forming composition.

FIG. 3 shows the release of a quaternary ammonium compound (QAC) over time from films sprayed from three liquid compositions of the invention on stainless steel coupons, then dried and submerged into water.

DETAILED DESCRIPTION

When an amount, concentration, or other value or parameter is given either as a range, preferred range, or a list of upper preferable values and lower preferable values, this is to be understood as specifically disclosing all ranges formed from any pair of any upper range limit or preferred value and any lower range limit or preferred value, regardless of whether ranges are separately disclosed. Where a range of numerical values is recited herein, unless otherwise stated, the range is intended to include the endpoints thereof, and all integers and fractions within the range. It is not intended that the scope of the invention be limited to the specific values recited when defining a range.

There has been a longstanding need for antimicrobial agents having improved antimicrobial efficacy and improved speed of action. The specific requirements for such agents vary according to the intended application (e.g., sanitizer, disinfectant, sterilant, aseptic packaging treatment, etc.) and the applicable public health requirements. For example, as set out in Germicidal and Detergent Sanitizing Action of Disinfectants, Official Methods of Analysis of the Association of Official Analytical Chemists, paragraph 960.09 and applicable sections, 15th Edition, 1990 (EPA Guideline 91-2), a sanitizer should provide a 99.999% reduction (5-log order reduction) within 30 seconds at room temperature, 25.+−0.2.degree. C., against several test organisms. The term "antimicrobial" as used herein includes agents capable of killing microorganisms, blocking or preventing microbial contamination (such as a forming a barrier), or suppressing or preventing growth of microorganisms, trapping microorganisms for killing, or preventing biofilm formation. The term "sanitizer" as used herein means an agent which reduces the number of microbial contaminants to safe levels as judged by public health requirements. According to an official sanitizer test, a sanitizer is a chemical that kills 99.999% of the specific test microorganisms in 30 seconds under the conditions of the test (EPA policy DIS/TSS-4: "Efficacy data requirements—Sanitizing rises for previously cleaned food-contact surfaces", United States Environmental Protection Agency, Jan. 30, 1979).

The term "disinfectant" as used herein means an agent which provides antimicrobial activity. According to an official disinfectant test, a disinfectant is a chemical that kills 99.9% of the specific test microorganisms in 10 minutes under the conditions of the test. (Germicidal and Detergent Sanitizing Action of Disinfectants, Official Methods of Analysis of the Association of Official Analytical Chemists, paragraph 960.09 and applicable sections, 15th Edition, 1990 (EPA Guideline 91-2)). The term "ppm" as used herein means micrograms per gram.

The present invention relates to a method and composition for controlling microorganisms. Said method comprises coating a surface with a removable, antimicrobial film-forming composition. Specifically, the invention relates to a method of providing control of microorganisms at a locus comprising
  a) providing a removable liquid coating composition comprising:
    i) a film-forming water soluble or water-dispersible agent;
    ii) at least one antimicrobial agent;
    iii) an inert solvent; and
    iv) a surfactant that lowers the surface tension of the liquid coating composition below 40 mN/m; and
  b) applying said composition to the locus.

The coating can be removed with an aqueous solution at a temperature of about 15° C. to about 100° C., or more preferably at a temperature of about 30° C. to about 80° C.

A locus of the invention comprises part or all of a target surface suitable to be coated. Target surfaces include all surfaces that can potentially be contaminated with microorganisms, including surfaces typically difficult to apply a film or coating to (such as hard-to-reach surfaces). Examples of target surfaces include equipment surfaces found in the food or beverage industry (such as tanks, conveyors, floors, drains, coolers, freezers, refrigerators, equipment surfaces, walls, valves, belts, pipes, drains, joints, crevasses, combinations thereof, and the like); building surfaces, including buildings under construction, new home construction, and surfaces in or on seasonal properties like vacation home surfaces (such as walls, wood frames, floors, windows), kitchens (sinks, drains, counter-tops, refrigerators, cutting boards), bathrooms (showers, toilets, drains, pipes, bathtubs), (especially for mold removal), decks, wood, siding and other home exteriors, asphalt shingle roofing, patio or stone areas (especially for algae treatment); boats and boating equipment surfaces; garbage disposals, garbage cans and dumpsters or other trash removal equipment and surfaces; non-food-industry related pipes and drains; surfaces in hospital, surgery or out-patient centers or veterinary surfaces (such as walls, floors, beds, equipment, clothing worn in hospital/veterinary or other healthcare settings, including scrubs, shoes, and other hospital or veterinary surfaces) first-responder or other emergency services equipment and clothing; lumber-mill equipment, surfaces and wood products; restaurant surfaces; supermarket, grocery, retail and convenience store equipment and surfaces; deli equipment and surfaces and food preparation surfaces; brewery and bakery surfaces; bathroom surfaces such as sinks, showers, counters, and toilets; clothes and shoes; toys; school and gymnasium equipment, walls, floors, windows and other surfaces; kitchen surfaces such as sinks, counters, appliances; wooden or composite decks, pool, hot tub and spa surfaces; carpet; paper; leather; animal carcasses, fur and hides; surfaces of barns, or stables for livestock, such as poultry, cattle, dairy cows, goats, horses and pigs; and hatcheries for poultry or for shrimp. Additional surfaces also include food products, such as beef, poultry, pork, vegetables, fruits, seafood, combinations thereof, and the like.

Additional loci suitable for use in the present invention comprise fibrous substrates and include fibers, yarns, fabrics, textiles, nonwovens, carpets, leather, or paper. The fibrous substrates are made with natural fibers such as wool, cotton, jute, sisal, sea grass, paper, coir and cellulose, or mixtures thereof; or are made with synthetic fibers such as polyamides, polyesters, polyolefins, polyaramids, acrylics and blends thereof; or blends of at least one natural fiber and at least one synthetic fiber. By "fabrics" is meant natural or synthetic fabrics, or blends thereof, composed of fibers such as cotton, rayon, silk, wool, polyester, polypropylene, polyolefins, nylon, and aramids such as "NOMEX®" and "KEVLAR®." By "fabric blends" is meant fabric made of two or more types of fibers. Typically these blends are a combination of at least one natural fiber and at least one synthetic fiber, but also can be a blend of two or more natural fibers or of two or more synthetic fibers. Nonwoven substrates include, for example, spunlaced nonwovens, such as SONTARA available from E. I. du Pont de Nemours and Company (Wilmington, Del., USA), and laminated nonwovens, such as spunbonded-meltblown-spunbonded nonwovens.

Examples of surface materials are metals (e.g., steel, stainless steel, chrome, titanium, iron, copper, brass, aluminum, and alloys thereof), minerals (e.g., concrete), polymers and plastics (e.g., polyolefins, such as polyethylene, polypropylene, polystyrene, poly(meth)acrylate, polyacrylonitrile, polybutadiene, poly(acrylonitrile, butadiene, styrene), poly(acrylonitrile, butadiene), acrylonitrile butadiene; polyesters such as polyethylene terephthalate; and polyamides such as nylon). Additional surfaces include brick, tile, ceramic, porcelain, wood, vinyl, and linoleum.

Equipment or surfaces protected with a temporary coating can be in use or not in use while protected. The target surface can be hydrophobic or hydrophilic. The antimicrobial, removable coating composition useful for the invention can be used as a replacement for standard sanitation products (such as diluted quaternary ammonium compound solutions, peracid foams, and the like), and can be used for daily sanitation as protective coatings for equipment in use or not-in use as well as for longer term protection (weeks or months).

Use of the antimicrobial, removable coating composition provides several advantages. The coating composition provides antimicrobial efficacy in a number of ways, including, but not limited to killing (both loose microorganisms and biofilms), reducing the growth of, or preventing the growth of microorganisms, by preventing the formation of biofilms, and by trapping microorganisms in, beneath or attached to the coating.

Application of the coating composition also reduces water usage because a concentrate of antimicrobial agent is directly applied in a thin film, and the antimicrobial agent can be maintained in higher concentrations and for longer periods of time at the substrate. In addition, labor can be reduced because the antimicrobial coating is applied once and removed in a later process step. The coating composition can be modified by formulating the composition with flow modifiers to coat hard-to-reach surfaces. This enables application of the antimicrobial agent to surfaces on or in equipment otherwise not accessible by application of conventional antimicrobial solutions with traditional shear-viscosity profiles. Horizontal and vertical surfaces can be covered with a thin layer of protective coating without waste of antimicrobial agent. By formulating compositions with appropriate flow modification and degree of cross-linking, coating compositions with various coating properties can be prepared that will vary in the degree of surface finish and protection as well as ease of removal.

In one embodiment of the invention, the antimicrobial, removable coating composition useful for the invention is applied to equipment, for example, in the food, dairy, or beverage industries, during shutdown periods of the equipment. When the equipment is started up, the coating is removed by a method described herein. In another embodiment, the antimicrobial, removable coating composition is used for sanitation of surfaces, such as surfaces of equipment of the food or beverage industry, for daily or weekly sanitation purposes. In yet another embodiment, fruit surfaces can be coated with the removable coating composition to prevent microbial spread and cross-contamination in food processing facilities. In still another embodiment, hospital walls, beds, and other hospital surfaces can be coated with the antimicrobial, removable coating composition useful for the invention. In another embodiment drains are coated with the removable coating composition. In another embodiment, building surfaces, such as in new home construction, walls or other surfaces are coated for prevention of mold contamination or mold removal.

The coating composition offers several mechanisms of protection towards contamination of microbial or non-microbial origin, such as soiling.

First, as the fluid composition is applied, planktonic or loosely adhering cells on the surface are killed (or growth is reduced or prevented) by the antimicrobial agent in the coating formulation.

Second, cells harbored by biofilms on the surface will be killed (or growth will be reduced or prevented) by diffusion of the antimicrobial(s) from the fluid coating into the hydrated biofilm. As the antimicrobial coating dries, the antimicrobial agent is likely to remain active because of the high water content retained at the interface between biofilm and antimicrobial coating. Due to the film being semi-permeable, the antimicrobial agent is mobile within the film contributing to a more effective barrier and longer lasting activity. The antimicrobial film thus formed constitutes a reservoir of antimicrobial agent providing much longer contact time than conventional sanitary rinse solutions typically drip off within seconds or minutes.

Third, planktonic cells reaching the antimicrobial coating from outside, after application of the antimicrobial coating, will be killed (or growth will be reduced or prevented) by the antimicrobial agent. Again, the antimicrobial coating will act as a reservoir of antimicrobial agent maintaining its microbiocidal properties until it is exhausted from the coating. This mechanism will also prevent biofilms from growing on the antimicrobial coating until the antimicrobial agent has been exhausted from the coating. The term "biofilm" refers to a collection of microorganisms (either one species, or multiple species) surrounded by a matrix of extracellular polymers (i.e., exopolymers or glycocalyx). These extracellular polymers are typically polysaccharides, but they can contain other biopolymers as well, and they can be attached to either an inert or living surface. Typical biofilm microorganisms are Gram positive and/or Gram negative bacteria, acting as pathogens, indicator organisms, and/or spoilage organisms.

Fourth, the coating constitutes a physical barrier for microorganisms, soil, fat and other matter. These solid contaminants will remain on the surface of the coating and will wash off at the time of removal of the coating.

A fifth protection mechanism occurs in situations in which the coating traps microorganisms so that they cannot reach or permeate a target surface and contaminate it. FIG. 1 illustrates various protection mechanisms described above. The protection mechanisms can operate individually, or simultaneously in any combination, depending on environmental conditions.

The long lasting activity while the coating is present on the locus is especially beneficial in a variety of applications. This residual benefit is far superior to antimicrobial agents such as a rinse solution that drips off quickly, or an agent that is subject to removal by touching or minor abrasion of the surface after application. The variation of film flexibility, viscosity, strength, and adhesion of the coating of the present invention permits it to be tailored to specific applications, thus making sustained antimicrobial protection available in numerous situations where such sustained activity (residual benefit) was not previously available.

Components of the Composition

The following provides a detailed description of the components of the compositions described herein.

Film-Forming Water Soluble or Water Dispersible Agent:

The film-forming water soluble or water dispersible agent can be at least one of any agent, as described below, that is durable and removable. The film or coating is removable, for instance, when subjected to an aqueous solution treatment above 15° C., preferably above 30° C. Examples include, but are not limited to, polyvinyl alcohols, polyvinyl alcohol copolymers, polyvinyl pyrrolidones, polyacrylic acid, acrylate copolymers, ionic hydrocarbon polymers, and polyurethanes, or combinations thereof.

Polyvinyl Alcohol and Copolymers Thereof

Polyvinyl alcohol, sometimes referred to as poly(vinyl alcohol), is made from polyvinyl acetate by hydrolysis. The physical properties of polyvinyl alcohol are controlled by the molecular weight and the degree of hydrolysis. The most commonly available grades of polyvinyl alcohol, ranked by degree of hydrolysis, are an 87-89% grade (containing 11-13 mole % residual vinylacetate units), a 96% hydrolysis grade (containing 4 mole % residual vinyl acetate units), and the "fully hydrolyzed" and "superhydrolyzed" grades, which are about 98% and greater-than-99% hydrolyzed, respectively. Lower degrees of hydrolysis (e.g. 74% and 79%) are also commercially available. Some preferred degrees of hydrolysis are greater than 85 mole %, or greater than 92 mole %. The polyvinyl alcohol component of the present invention can also be a copolymer of vinyl alcohol, such as one obtained by hydrolyzing a copolymer of vinyl acetate with small amounts (up to about 15 mole %) of other monomers. Suitable co-monomers are e.g. esters of acrylic acid, methacrylic acid, maleic or fumaric acids, itaconic acid, etc. Also, copolymerization of vinyl acetate with hydrocarbons e.g. alpha-olefins such as ethylene, propylene or octadecene, etc., with higher vinyl esters such as vinyl butyrate, 2-ethyl hexoate, stearate, trimethyl acetate, or homologues thereof ("VV-10" type of vinyl esters sold by Shell Chem. Co.), etc. gives copolymers that can be hydrolyzed to suitable polyvinyl alcohol copolymers. Other suitable comonomers are N-substituted acrylamides, vinyl fluoride, allyl acetate, allyl alcohol, etc. Also the free unsaturated acids such as acrylic acid, methacrylic acid, monomethyl maleate, etc. can act as comonomers.

Because of the variety of grades either known in the literature or commercially available, one skilled in the art can formulate a polyvinyl alcohol solution having an average degree of hydrolysis ranging from 74 to more than 99% simply by blending the known or commercial grades in any desired ratios. Accordingly, the term "partially hydrolyzed grade polyvinyl alcohol", as used in this description should be understood to include both a single grade and a mixture of grades, and the term "average degree of hydrolysis" should be understood to refer to the degree of hydrolysis arrived at by averaging (with appropriate weighting on the basis of proportions) the partially hydrolyzed grades in the mixture, if a mixture is used, or the average degree of hydrolysis of a single grade, if a single grade is used (an "88% grade", for example, may be the average of a spectrum ranging from 87 to 89% within the same grade).

Variation of film flexibility, water sensitivity, ease of solvation, viscosity, film strength and adhesion of the polyvinyl alcohol film can be varied by adjusting molecular weight and degree of hydrolysis. In one embodiment, the polyvinyl alcohol for use in the process of this invention has a degree of hydrolysis from about 85% to greater than 99%. In another embodiment, the polyvinyl alcohol has a degree of hydrolysis from about 92% to greater than 99%. In one embodiment, the polyvinyl alcohol has a number-averaged molecular weight (Mn) that falls in the range of between about 4,000 to about 200,000, or about 4,000 to about 186,000, or 30,000 to about 186,000. In another embodiment, the polyvinyl alcohol has a molecular weight that falls in the range of between about 70,000 and 130,000. In another embodiment, the polyvinyl alcohol of various molecular weights can be blended to give the desired properties. In one embodiment, the polyvinyl alcohol is used at about 2% to about 30% by weight of the weight of the solution. In a more specific embodiment, the polyvinyl alcohol is used at about 2% to about 15% by weight of the weight of the solution. In an even more specific embodiment, the polyvinyl alcohol is used at about 3% to about 6% by weight of the weight of the solution.

Polyvinylpyrrolidone (PVP)

The film-forming composition of the present invention can contain PVP at a concentration of about 0.25 to about 50% by weight. Suitable grades of PVP are available from International Specialty Products (Wayne, N.J., USA). Such grades include: K-15, having a molecular weight range of about 6,000 to about 15,000; K-30, having a molecular weight range of about 40,000 to about 80,000; K-60, having a molecular weight range of about 240,000 to about 450,000; K-90, having a molecular weight range of about 900,000 to about 1,500,000; and K-120, having a molecular weight range of about 2,000,000 to about 3,000,000. Mixtures of PVP's can be employed, as can combinations of PVP and other film-forming compounds.

The amount and molecular weight distribution of the PVP used will influence the viscosity, coverage, and cost of the final product. The viscosity should preferably be between about 20 to about 1000 centipoise, and more preferably between about 20 to 100 centipoise. Typically, lower molecular weight PVP will give a less viscous product than a higher molecular weight PVP at the same concentration. For a given concentration of PVP, as the molecular weight range increases, the viscosity will also increase. The present invention can employ PVP having any of a number of molecular weight ranges. For example, film-forming compositions can utilize the PVP grades K-15, K-30, K-60, K-90, or K-120 described above. It is preferred, however, to use PVP with a molecular weight distribution between about 15,000 and about 3,000,000. PVP having this molecular weight distribution typically gives a film-forming composition with a viscosity, which can be easily adjusted and washes off a surface easily with no visible signs of interaction with a painted surface. In a preferred embodiment, PVP with a molecular weight distribution between about 15,000 and about 3,000,000 is present at a concentration of between about 0.25% and about 40% by weight. In another preferred embodiment, PVP with a molecular weight distribution between about 60,000 and about 1,200,000 is present at a concentration of between about 2% and about 30% by weight.

Polyacrylate

The film-forming compositions of the invention can also include an acrylate emulsion polymer. Preferred acrylate polymers are those composed of one or more copolymers of ethylenically unsaturated comonomers. The monomers useful in the compositions of the invention comprise one or more ethylenically unsaturated polar or non-polar, non-ionizing monomers and at least one ethylenically unsaturated carboxylic acid. The monomers can include more than one ethylenically unsaturated sites and the suitable carboxylic acids preferably include one or more carboxyl groups. Suitable ethylenically unsaturated acids include acrylic, methacrylic, butenoic, maleic, fumaric, itaconic, and cinnamic acids as well as dimer acids such as acrylic and methacrylic dimer acids and combinations of the foregoing. Ethylenically unsaturated polar or non-polar, non-ionizing monomers include ethylenically unsaturated esters, ethylenically unsaturated nitriles, ethylenically unsaturated alcohols, aryl vinyl compounds and arylalkyl vinyl compounds. Based on commercial availability, the acrylate polymers are preferably copolymers of acrylic acid esters and methacrylic acid esters, such as C1 to C6 alkyl acrylates or methacrylates, in combination with acrylic or methacrylic acid, cyanoacrylates and methacrylates (e.g., acrylonitrile) and other known acrylic, vinyl and diene monomers. The acrylate polymer component can optionally contain one or more metal salt complexing agents effective as cross-linking agents. When present such complexing agents bond with the pendant carboxyl groups on the acrylate polymers to form a cross-linked polymer, which is more water resistant than a comparable acrylate polymer which is not cross-linked. Suitable metal salt complexing agents include those containing zinc such as zinc ammonium carbonate, for example. Other useful complexing agents include known salts of various metals including zirconium, calcium, magnesium and the transition metals, for example. Exemplary complexing agents include polyvalent metal complexes such as ammonium zinc carbonate, ammonium calcium ethylenediamine carbonate, ammonium zinc acetate, ammonium zinc acrylate, ammonium zinc maleate, ammonium zinc amino acetate and ammonium calcium aniline and combinations of the foregoing.

Commercially available carboxylated acrylate polymer emulsions can be used either alone or in combination with one another in the film-forming compositions of the invention. Suitable commercial emulsions include those with a metal complexing agent as described above as well as those without added metal complexing agents. Suitable metal free emulsions include commercially available materials such as those available under the trade names of "Rhoplex" NT 2624 (Rohm and Haas Company, Philadelphia, Pa.); "Esi-Cryl" 20/20 (Emulsion Systems, Valley Stream, N.Y., USA); and "Syntran" 1905 (Interpolymer of Canton, Mass., USA). Commercial emulsions which include a zinc complexing agent suitable for inclusion in the compositions of the invention include those available under the trade designations "Duraplus" I and "Rhoplex" B-825 (both from Rohm and Haas), "Conlex" V (Morton International, Chicago, Ill., USA) and "Esi-Cryl" 2000 (Emulsion Systems Ltd., Valley Stream, N.Y., USA). Other metal containing and metal free acrylate emulsions can be used, as known by those skilled in the art.

The acrylate polymer component is preferably prepared as an emulsion and is present in the film-forming composition of the invention at a concentration ranging from about 0.25 to 30 wt %, and more preferably from about 2 to 20 wt % based on total weight of the composition.

Ionic Hydrocarbon Copolymers

Ionic hydrocarbon copolymers useful for the present invention include a polymer of an α-olefin having the general formula $RCH=CH_2$ where R is a radical selected from the class consisting of hydrogen and alkyl radicals having from 1 to 8 carbon atoms, the olefin content of said polymer being at least 50 mol % based on the polymer, and an α, β-ethylenically unsaturated carboxylic acid having 1 or 2 carboxylic groups, the acid monomer content of said polymer being from 0.2 to 25 mol % based on the polymer. This type of polymer is described in U.S. Pat. No. 3,264,272, specifically incorporated herein by reference.

Polyurethane Dispersion:

A polyurethane dispersion or solution refers to an aqueous dispersion or solution of a polymer containing urethane groups. A cross-linked polyurethane dispersoid refers to an aqueous dispersion of a polymer containing urethane groups and cross-linking, as those terms are understood by persons of ordinary skill in the art. Depending on the degree of cross-linking, the polyurethane may be an aqueous solution (no cross-linking or low cross-linking) or an aqueous dispersion.

Cross-linked polyurethane dispersions are described in the U.S. Patent Application 2005/0215663, herein incorporated specifically by reference. These polymers can incorporate hydrophilic functionality to the extent required to maintain stable dispersion of the polymer in an aqueous solution. These polymers can also incorporate ionic and nonionic functionality to the extent required to maintain a stable dispersion of the polymer in water. Alternatively, these polymers can be prepared by emulsification of hydrophobic polyurethanes in water with the aid of suitable external emulsifiers, surfactants and the like, and/or utilizing strong shear forces to form an oil-in-water dispersion.

In general, the stability of the cross-linked polyurethane in the aqueous vehicle is achieved by incorporating anionic, cationic and/or non-ionic components in the polyurethane polymer, which facilitates stabilizing the cross-linked polyurethane in aqueous systems. The amount of cross linking is chosen to give the desired water resistance. External emulsifiers can also be added to stabilize the polyurethane. Combinations of incorporated anionic, cationic and/or non-ionic components, and/or external emulsifiers can also be used.

Antimicrobial Agent:

The antimicrobial agent useful for the invention can be either an inorganic or organic agent, or a mixture thereof. The invention is not to be limited to the selection of any particular antimicrobial agent, and any known water-soluble or water-dispersible antimicrobial may be included in the compositions of the invention such as antimicrobials, mildewcides, antiseptics, disinfectants, sanitizers, germicides, algicides, antifouling agents, preservatives, and combinations of the foregoing and the like provided that the antimicrobial agent is chemically compatible with other components in the composition. Suitable classes of antimicrobial agents are described below.

The term "inorganic antimicrobial agent" used herein is a general term for inorganic compounds which contain a metal or metal ions, such as silver, zinc, copper and the like which have antimicrobial properties. The term "organic antimicrobial agent" used herein is the general term for natural extracts, low molecular weight organic compounds and high molecular weight compounds all of which have antimicrobial properties and which generally contain nitrogen, sulfur, phosphorus or like elements. Examples of useful natural antimicrobial agents are chitin, chitosan, antimicrobial peptides such as nisin, lysozymes, wasabi extracts, mustard extracts, hinokitiol, tea extracts and the like. High molecular weight compounds having anti-microbial properties include those having an ammonium salt group, phosphonium salt group, sulfonium salt group or like onium salts, a phenylamide group, diguanide group attached to a straight or branched polymer chain, for example phosphonium salt-containing vinyl polymers, as are known in the art (E.-R. Kenawy and Y. A. -G. Mahmoud "Biologically active polymers, 6: Synthesis and antimicrobial activity of some linear copolymers with quaternary ammonium and phosphonium groups" in Macromolecular Bioscience (2003), 3(2), 107-116).

Examples of useful low molecular weight antimicrobial agents include chlorhexidine, chlorhexidine gluconate, glutaral, halazone, hexachlorophene, nitrofurazone, nitromersol, thimerosol, C1-C5-parabens, hypochlorite salts, clofucarban, clorophen, phenolics, mafenide acetate, aminacrine hydrochloride, quaternary ammonium salts, chlorine and bromine release compounds (e.g. alkali and alkaline earth hypochlorites and hypobromites, isocyanurates, chlorinated derivatives of hydantoin, sulfamide, amine, etc.), peroxide and peroxyacid compounds (e.g. peracetic acid, peroctanoic acid), protonated short chain carboxylic acids, oxychlorosene, metabromsalan, merbromin, dibromsalan, glyceryl laurate, sodium and/or zinc pyrithione, trisodium phosphates, (dodecyl)(diethylenediamine)glycine and/or (dodecyl)(aminopropyl)glycine and the like. Useful quaternary ammonium salts include the N-C10-C24-alkyl-N-benzyl-quaternary ammonium salts which comprise water solubilizing anions such as halide, e.g., chloride, bromide and iodide; sulfate, methosulfate and the like and the heterocyclic imides such as the imidazolinium salts. Useful phenolic germicides include phenol, m-cresol, o-cresol, p-cresol, o-phenyl-phenol, 4-chloro-m-cresol, chloroxylenol, 6-n-amyl-m-cresol, resorcinol, resorcinol monoacetate, p-tert-butylphenol and o-benzyl-p-chlorophenol. Useful antimicrobial agents known to be effective in preventing the visible growth of mildew colonies, include, for example, 3-iodo-2-propynl butylcarbamate, 2-(4-thiazolyl)benzimidazole, diiodomethyl-p-tolylsulfone, tetrachloroisophthalonitrile, the zinc complex of 2-pyridinethiol-1-oxide (including salts thereof) as well as combinations of the foregoing.

The coating composition comprising the antimicrobial agent offers protection against diverse microorganisms. The term "microorganism" is meant to include any organism comprised of the phylogenetic domains of bacteria and archaea, as well as unicellular (e.g. yeasts) and filamentous (e.g. molds) fungi, unicellular and filamentous algae, unicellular and multicellular parasites, viruses, virinos and viroids.

In one embodiment, the coating composition protects against Gram positive or Gram negative bacteria. Gram positive bacteria which are inhibited or killed by the coating include, but are not limited to, *Mycobacterium tuberculosis, M. bovis, M. typhimurium, M. bovis* strain BCG, BCG substrains, *M. avium, M. intracellulare, M. africanum, M. kansasii, M. marinum, M. ulcerans, M. avium* subspecies *paratuberculosis, Staphylococcus aureus, S. epidermidis, S. equi, Streptococcus pyogenes, S. agalactiae, Listeria monocytogenes, L. ivanovii, Bacillus anthracis, B. subtilis, Nocardia asteroides*, and other *Nocardia species, Streptococcus viridans* group, *Peptococcus* species, *Peptostreptococcus* species, *Actinomyces israelii* and other *Actinomyces species, Propionibacterium acnes*, and *Enterococcus species*. Gram negative bacteria which are inhibited or killed by the coating include, but are not limited to, *Clostridium tetani, C. perfringens, C. botulinum*, other *Clostridium* species, *Pseudomonas aeruginosa*, other *Pseudomonas* species, *Campylobacter* species, *Vibrio cholerae, Ehrlichia* species, *Actinobacillus pleuropneumoniae, Pasteurella haemolytica, P. multocida*, other *Pasteurella* species, *Legionella pneumophila*, other *Legionella* species, *Salmonella typhi*, other *Salmonella* species, *Shigella* species *Brucella abortus*, other *Brucella* species, *Chlamydia trachomatis, C. psittaci, Coxiella burnetti, Escherichia coli, Neiserria meningitidis, N. gonorrhea, Haemophilus influenzae, H. ducreyi*, other *Haemophilus* species, *Yersinia pestis, Y. enterolitica*, other *Yersinia* species, *Escherichia coli, E. hirae* and other *Escherichia* species, as well as other *Enterobacteriacae, Brucella abortus* and other *Brucella* species, *Burkholderia cepacia, B. pseudomallei, Francisella tularensis, Bacteroides fragilis, Fusobacterium nucleatum, Provetella* species, *Cowdria ruminantium, Klebsiella* species, and *Proteus* species. In another embodiment, the coating provides protection against fungi, including but not limited to, *Alternaria alternata, Aspergillus niger, Aureobasidium pullulans, Cladosporium cladosporioides, Drechslera australiensis, Gliomastix cerealis, Monilia grisea, Penicillium commune, Phoma fimeti, Pithomyces chartarum*, and *Scolecobasidium humicola*.

Enzymes:

Enzymes useful for the present invention include those that have beneficial effects such as cleaning, destaining, and biofilm degradation. These enzymes include one or a mixture of: deacetylase, amidase, cellulase, esterase, glycosidase, xylanase, amylase, transaminase, laminarinase, beta-galactosidase, beta-mannosidase, pullulanase, phosphatase, protease, lipase, and perioxidase.

Surfactants:

The compositions useful for the present invention can also contain one or more surfactants. While not being bound by theory, it is believed that a surfactant will aid wefting of the surface to be covered and will aid even coverage by the film. The surfactant is also believed to aid foaming by the film when removed, thereby aiding removal of the film and washing of the protected surface. Suitable surfactants have a preferred hydrophilic-lipophilic balance (HLB) of from about 9 to about 17. Suitable surfactants include, but are not limited to: amphoteric surfactants, such as Amphoteric N from Tomah Products; silicone surfactants, such as BYK 348 available from BYK Chemie (BYK-Chemie GmbH, Wesel; Germany); fluorinated surfactants such as Zonyl® FS300 from DuPont (DuPont, Wilmington, Del., USA); and nonylphenoxypolyethoxyethanol based surfactants, such as Triton N-101 available from Dow (Midland, Mich., USA). Other suitable surfactants include ethoxylated decynediols such as Surfynol 465 available from Air Products & Chemicals (Allentown, Pa., USA); alkylaryl polyethers such as Triton CF-10 available from Dow; octylphenoxy polyethoxy ethanols such as Triton X-100 available from Dow; ethoxylated alcohols such as Neodol 23-5 or Neodol 91-8 available from Shell (The Hague, the Netherlands); Tergitol 15-S-7 available from Dow, Steol-4N, a 28% sodium laureth sulfate from Stepan Company (Northfield, Ill., USA), sorbitan derivatives such as Tween 20 or Tween 60 from Uniqema (New Castle, Del., USA), and quaternary ammonium compounds, such as benzalkonium chloride.

Other suitable surfactants include organo-silicone surfactants such as Silwet®L-77 from Setre Chemical Company (Mephis, Tenn., USA), DowCorning® Q2-5211 from DowCorning Silicones (Midland, Mich., USA), or Silsurf® A008 by Siltech Corporation (Toronto, ON, Canada).

The preferred range for use of the surfactant is from about 0.001 to about 1 wt % of the formulation, and more preferably from about 0.01 to about 0.2 wt %.

Solvents:

Inert solvents useful for the invention include water. Additional solvents include mono alcohols monofunctional and polyfunctional alcohols, preferably containing from about 1 to about 6 carbon atoms and from 1 to about 6 hydroxy groups. Examples include ethanol, isopropanol, n-propanol, 1,2-propanediol, 1,2-butanediol, 2-methyl-2,4-pentanediol, mannitol and glucose. Also useful are the higher glycols, polyglycols, polyoxides, glycol ethers and propylene glycol ethers. Additional solvents include the free acids and alkali metal salts of sulfonated alkylaryls such as toluene, xylene, cumene and phenol or phenol ether or diphenyl ether sulfonates; alkyl and dialkyl naphthalene sulfonates and alkoxylated derivatives.

Additional Components:

Additional components that can be added to the coating composition include colorants, rheology modifiers, cross-linking agents, plasticizers, surfactants, solubilizing agents, antioxidants, pH adjusters, wetting agents, antifoaming agents, extenders, lubricants, processing aids, color fastness agents, and additional performance-enhancing agents. Wetting agents lower the surface tension of the formulation to allow it to wet the surfaces, spread on the surfaces and potentially penetrate into, under, and around soils, solid matter, microorganisms, biofilms, surface contaminations, fat and surface crevices.

Colorants:

Colorants useful for the present invention include dyes and pigments such as food grade pigments.

Dyes useful for the invention include both water soluble and water insoluble dyes. Water soluble dyes can be formulated easily in the aqueous systems of the invention. Water insoluble dyes can be included in an oil phase that can be dispersed or suspended in the antimicrobial coating compositions useful for the invention. Useful dyes for the purpose of this invention are typically organic compounds that absorb visible light resulting in the appearance of a detectable color. Fluorescent dyes can also be used, for example, for purposes of visualizing a film by ultraviolet light.

For the food processing industry, including restaurant surfaces, and for fruit, in one embodiment of the invention common FD&C approved dyes can be used since these materials are typically approved for use as direct additives for food stuffs. The dyes typically useful in this invention are colorants approved for use in foods, drugs, cosmetics and medical devices.

Colorants currently in use and their status follow. Colorants permitted in foods that are (1) subject to certification: FD&C Blue No. 1, FD&C Blue No. 2, FD&C Green No. 3, FD&C Red No. 3, FD&C Red No. 40, FD&C Yellow No. 5, FD&C Yellow No. 6, Citrus Red No. 2, and Orange (B) (2) exempt from certification: annatto extract, theta-apo-8'-carotenal, canthaxanthin, caramel, theta-carotene, carrot oil, cochineal extract (carmine), corn endosperm oil, dehydrated beets (beet powder), dried algae meal, ferrous gluconate, fruit juice, grape color extract, grape skin extract, paprika, paprika oleoresin, riboflavin, saffron, synthetic iron oxide, tagetes meal and extract, titanium dioxide, toasted partially defatted cooked cottonseed flour, turmeric, termeric oleoresin, ultramarine blue, and vegetable juice. Colorants permitted in drugs (including colorants permitted in foods) that are (1) subject to certification: FD&C Red No. 4, D&C Blue No. 4, D&C Blue No. 9, D&C Green No. 5, D&C Green No. 6, D&C Green No. 8, D&C Orange No. 4, D&C Orange No. 5, D&C Orange No. 10, D&C Orange No. 11, D&C Red No. 6, D&C Red No. 7, D&C Red No. 17, D&C Red No. 21, D&C Red No. 22, D&C Red No. 27, D&C Red No. 28, D&C Red No. 30, D&C Red No. 31, D&C Red No. 33, D&C Red No. 34, D&C Red No. 36, D&C Red No. 39, D&C Violet No. 2, D&C Yellow No. 7, D&C Yellow No. 8, D&C Yellow No. 10, D&C Yellow No. 11, and Ext. D&C Yellow No. 7. Additionally cantaxanthin, beta carotene, chlorophyllin, and other colors are known.

For a more detailed listing and/or discussion on approved colors, see D. M. Marmion, Handbook of U.S. Colorants, Foods, Drugs, Cosmetics and Medical Devices, John Wiley & Sons Inc., New York (1991) and U.S. Code of Federal Regulations, Title 21, parts 70-82.

Rheology Modifiers:

The composition useful for the invention can also contain one or more rheology modifiers, or rheology agents, employed to enhance viscosity, or thicken and cause the aqueous treatment or coating composition to cling to the surface. Clinging enables the composition to remain in contact with transient and resident microorganisms for longer periods of time, promoting microbiological efficacy and resisting waste because of excessive dripping. The rheology modifier can be a film former or act cooperatively with a film-forming agent to form a barrier that provides additional protection. Water soluble or water dispersible rheology modifiers that are useful can be classified as inorganic or organic. The organic thickeners can further be divided into natural and synthetic polymers with the latter still further subdivided into synthetic natural-based and synthetic petroleum-based.

Inorganic thickeners are generally compounds such as colloidal magnesium aluminum silicate (VEEGUM®), colloidal clays (Bentonites), or silicas (CAB-O-SIL®) which have been fumed or precipitated to create particles with large surface to size ratios. Natural hydrogel thickeners of use are primarily vegetable derived exudates. For example, tragacanth, karaya, and acacia gums; and extractives such as carrageenan, locust bean gum, guar gum and pectin; or, pure culture fermentation products such as xanthan gum are all potentially useful in the invention. Chemically, all of these materials are salts of complex anionic polysaccharides. Synthetic natural-based thickeners having application are cellulosic derivatives wherein the free hydroxyl groups on the linear anhydro-glucose polymers have been etherified or esterified to give a family of substances which dissolve in water and give viscous solutions. This group of materials includes the alkyl and hydroxylalkylcelluloses, specifically methylcellulose, hydroxyethylmethylcellulose, hydroxypropylmethylcellulose, hydroxybutylmethylcellulose, hydroxyethylcellulose, ethylhydroxyethylcellulose, hydroxypropylcellulose, and carboxymethylcellulose. Another preferred group of thickeners include polyacrylates such as the proprietary Acusol thickeners, (e.g. Acusol 823, Rohm and Haas, Philadelphia, Pa., USA), and Carbopol thickeners, such as Carbopol 934 or Carbopol Aqua-30 Polymer (B F Goodrich, Cleveland, Ohio, USA). A polyacrylate thickener can be used at concentrations of up to about 3 wt % of the film former weight. Mixtures of thickening agents can also be employed where the total amount can be up to about 3 wt % depending on the thickeners used and the desired viscosity of the final product.

Other potential thickeners for this application include dextrin, cornstarch and hydrous magnesium silicates, such as sodium magnesium silicate sold under the trade name Laponite XLG (Southern Clay Products, Inc., Gonzales, Tex., USA).

Cross-Linking Agents:

The present invention may optionally include cross-linking agents. Advantages of using cross-linking agents with the film-forming composition include influencing the mechanical film properties, such as tackiness and mechanical strength, as well as solubility of the coating. In the present invention, cross-linked films yielded much more mechanically robust films. Furthermore, cross-linking decreases tackiness and prevents soil and microorganisms from physically adhering to the polymer film, which may be desirable for certain applications. In the present invention, cross-linking had a beneficial impact on release of the antimicrobial agent from the film. The degree of cross-linking is adjusted so to achieve the desired combination of properties.

Cross-linking agents suitable for use with polyvinyl alcohol and copolymers thereof include, but are not limited to: aldehydes (e.g. formaldehyde, glyoxal, glutaraldehyde), boric acid, sodium tetraborate, metal ions (e.g. ions of Zn, Fe, Al, Ni, V, Co, Cu, Zr, Ti, Mn), organometallic compounds (e.g. organic titanates such as DuPont Tyzor®, organic Cr(III) complexes such as DuPont Quilon®), siloxanes (e.g., tetraethoxysilane, polydimethylsiloxane), isocyanates (e.g. of the blocked, water-soluble or dispersed type), epoxides (e.g. diglycidyl ether), dicarboxylic acid (e.g., oxalic, maleic, fumaric, phthalic), urea based cross-linkers (e.g. Sunrez 700). Bi- and trivalent metal cations (e.g. Fe(II), Fe(III), Al(III)) are preferred because they provide the formation of a coordinative linkage between the PVOH polymer chains upon film drying. This allows the cross-linker to be added to the film-forming liquid in a 'one-pot' mixture. Care must be taken to choose an adequate concentration in order to efficiently cross-link the polymer without precipitating other ingredients such as particulate rheology control agents.

In most cases the cross-linking agent will be mixed with other ingredients using standard mixing techniques. The cross-linking reaction can optionally be carried out in the presence of a catalyst, as is well known to those skilled in the art. In the case of the aldehydes, isocyanates, siloxanes, diglycidyl ether, and dicarboxylic acid, heat and an acid catalyst or metal catalyst can be used additionally.

The cross-linking agent concentration in the formulation can be zero to an upper limit which is either determined by the stability limit of the formulation where precipitation starts to occur, or the inability of the resulting film to be removed efficiently. The preferred cross-linking agent concentration can depend strongly on the type of cross-linking agent used and is typically below 25 wt % of the polymer content, more preferably below 10 wt % of the polymer content.

Plasticizers:

It is important for flexibility and integrity of the protective film that the resultant film be plasticized. Plastization of the film has been accomplished for the purposes of this invention by the incorporation of a suitable plasticizing agent such as polyethylene glycol or glycerol. Other plasticizers suitable for the invention include, but are not limited, to solvents, polyols, polyethylene glycols of and average molecular weight between 200 and 800 g/mole and sorbitol. PEG is preferred over glycerol since glycerol is easily metabolized by microorganisms potentially resulting in microbial growth.

Inclusion of a plastisizer generally also allows the film to retain a slightly tacky surface feel. As the plastisizer level increases, the resulting film will also exhibit an increasing degree of tackiness. Such tackiness can be desirable at low levels in order to capture airborne particles and soil or other materials. If plastisizer levels are too high, however, the coating becomes too tacky and will show low resistance to accidental mechanical removal, by wiping, for example. The preferred plasticizer amount is from about 1.0 wt % to about 20 wt % of the weight of the film former, and more preferably from about 5 wt % to about 8 wt %.

Additional Performance-Enhancing Agents:

In addition to the foregoing components, the composition of the present invention can also comprise one or more performance enhancing additives, "performance enhancers". These include flash rust inhibitors, which include any of a number of organic or inorganic materials used in a water-based system to prevent rust from forming on contact with the material and bare metal. One example is sodium benzoate.

Another optional performance enhancing additive is one or more of an array of defoamers recommended for water-based systems, to prevent unwanted foaming (gas bubbles) of the product during application or after formation of the film or coating. Too much foam can disrupt the required continuous film formation of the product and result in product failure. It can also be advantageous to add a foam control product, to aid in mixing and processing the masking composition, such as Drewplus L475 from Ashland Chemical, Inc. Drew Industrial Division (Covington, Ky., USA). Furthermore, the liquid coating composition of the invention may be applied in the form of a foam to a locus whereby the composition serves as a temporary visual indicator that the surface has been covered. By the action of an antifoaming agent, the foam or gas bubbles are broken down, which is indicative of a dried film or coating. Thus, the antifoaming agent can be used in accordance with the invention as an indicator by an operator, letting the operator know that the film or coating has dried.

Additional optional performance enhancing additives are antioxidants to increase the shelf life of the coating formulation. One example is butylated hydroxytoluene. Additional additives include fragrances.

Foaming agents can additionally be added to create gas bubbles in the applied coating. Gas bubbles can function as an opacifying agent to facilitate the application and/or to allow for longer contact time with a surface e.g. by preventing dripping from an inclined surface and/or to reduce the amount of coating formulation needed to treat a certain surface area or volume.

Application indicators may also be added. Some of these are described above, but include pigments, dyes, fluorescent dyes or gas bubbles generated during application.

Small amounts (typically less than 1 percent by weight) of these additional materials can be added with an appropriate adjustment of the water or other components. It is to be understood that mixtures of any one or more of the foregoing optional components can also be employed.

For loci comprised of fibrous substrates, an optional performance-enhancing ingredient is an agent that provides a surface effect. Such surface effects include no iron, easy to iron, shrinkage control, wrinkle free, permanent press, moisture control, softness, strength, anti-slip, antistatic, anti-snag, anti-pill, stain repellency, stain release, soil repellency, soil release, water repellency, oil repellency, odor control, antimicrobial, or sun protection, Applying the Antimicrobial Coating Composition:

The film or coating can be applied to the target surface or locus by any means, including pouring. The film or coating is applied to achieve a continuous and/or homogenous layer on a target surface. Coating systems routinely used for paints and coatings, such as, but not limited to, brushes, rollers, paint pads, mats, sponges, combs, hand-operated pump dispensers, compressed air operated spray guns, airless spray guns, electric or electrostatic atomizers, backpack spray application equipment, clothes, papers, feathers, styluses, knives, and other applicator tools can be used for coating. If dipping is used as a method to apply the coating, no special equipment is required. For fibrous substrates, such as textiles and carpets, the coating can be applied by exhaustion, foam, flex-nip, nip, pad, kiss-roll, beck, skein, winch, liquid injection, overflow flood, roll, brush, roller, spray, dipping, immersion, and the like. The coating can also be applied by use of the conventional beck dyeing procedure, continuous dyeing procedure or thread-line application.

The coating system may also be one more components, and may include a catalyst.

In one embodiment of the invention, electrostatic sprayers can be used to coat the surface. Electrostatic sprayers impart energy to the aqueous coating composition via a high electrical potential. This energy serves to atomize and charge the aqueous coating composition, creating a spray of fine, charged particles. Electrostatic sprayers are readily available from suppliers such as Tae In Tech Co., South Korea and Spectrum, Houston, Tex., USA. Generally, the coating is allowed to set or dry for about greater than 5 minutes in order to form the film. However, the coating may be antimicrobially effective in a shorter time-frame, such as after 30 seconds. The coating may be removed before it is dried or anytime thereafter depending on the desired use. The drying time will be partially dependent on a number of factors, including environmental conditions such as humidity and temperature. The drying time will also depend on the thickness of the applied coating.

In another embodiment of the invention, an airless spray guns can be used to coat the target surface. Airless spray guns use high fluid pressures and special nozzles, rather than compressed air, to convey and atomize the liquid. The liquid is supplied to an airless gun by a fluid pump at pressures typically ranging from 500 to 6500 psi. When the paint exits the fluid nozzle at this pressure, it expands slightly and atomizes into tiny droplets without the impingement of atomizing air. The high velocity of the exiting paint propels the droplets toward the target surface. The fluid nozzle on an airless gun differs substantially from the fluid nozzle on an air atomized gun. Selection of the proper nozzle determines how much paint is delivered and the fan pattern of application. The size of the airless nozzle orifice determines the quantity of paint to be sprayed. Airless fluid delivery is high, ranging from 700-2000 mL/min. Recommended gun distance is 12 inches from the target, and depending upon the nozzle type, a fan pattern of 5 to 17 inches is possible. Thus, nozzles can be selected for each application based on the size and shape of the target surface and the thickness of the coating to be applied. Airless guns create little air turbulence that can repel the liquid from "hard to reach areas", such as would be found in food processing equipment, hatcheries etc. The high flow rate makes airless advantageous in cleaning and disinfecting situations, where the antimicrobial coating is to be applied over a large surface area and multiple surfaces. The thickness of the applied and dried film will depend on a variety of factors. These factors include the concentration of the film forming agent, the concentration of rheology control additives and/or other additives, as well as the application temperature and humidity. Film thickness and film uniformity also depend, at least in part, on parameters of the application equipment, such as fluid delivery, spray orifice diameter, air pressure or piston pump pressure in the case of airless application, and the distance of the spray applicator to the target surface. Therefore, the liquid formulation may be adjusted to yield the desired film thickness.

The atomization of the coating solution is chosen such that a thin film is applied homogeneously to the target area.

Generally, the coating is allowed to set or dry for about 5 to about 60 minutes in order to form the film. The present composition, when applied onto a surface, will form a film or a coating by evaporation of the inert solvent. The solvent evaporation could occur by allowing the coating to dry in place, or alternatively by blowing dry with heated or unheated air. However, the coating may be effective as an antimicrobial agent in a shorter time-frame, such as after 30 seconds. The coating may be removed before it is dried or anytime thereafter depending on the desired use. The drying time will be partially dependent on a number of factors, including environmental conditions such as humidity and temperature. The drying time will also depend on the thickness of the applied coating. The coating is preferably used at a thickness of about 0.3 to about 300 microns. In a more specific embodiment, the coating is used at a thickness of about 0.5 to about 100 microns. In an even more specific embodiment, the coating is used at a thickness of about 1.0 to about 30 microns.

Film or Coating Thickness:

The thickness of the film or coating applied onto the target surface influences the time needed for removal and the amount of biocide per unit area applied to the surface. Thicker films increase the time interval until the film has to be re-applied to maintain the desired antimicrobial properties. Thinner films will be easier and faster to remove by rinsing. It is thus important to apply the formulation in a fashion that results in a film thickness that allows both easy removal of the coating and long-lasting antimicrobial properties. As described above, the film or coating has a thickness of about 0.3 to about 300 microns. In a more specific embodiment, the film or coating has a thickness of about 0.5 to about 100 microns. In an even more specific embodiment, the film or coating has a thickness of about 1.0 to about 30 microns.

Film Removal:

This invention is directed to films that can be removed at a time determined appropriate by the user. The time of removal can be determined by either (i) the desired minimum contact time to allow for the desired antimicrobial activity, typically expressed as amount of killed or inactivated microorganisms out of a starting population or (ii) the need or desire to take the coating off the surface before starting a subsequent operation or process step. Although the coating can be removed any time, such as after drying, the film thickness, concentration of antimicrobial agent, and specific use determines the appropriate time for removal. For instance the user may wish to put treated equipment back into normal operation after a period of operational shutdown. Fruit, for example, will require washing prior to eating. Upon exhaustion of the biocide in the film, the film could be removed and a fresh coating layer could be applied. For example, drains can be treated periodically such as daily, weekly or biweekly. Antimicrobial activity can be measured as early as after 30 seconds, hours, days, weeks, months, even years after application of the film. Therefore, timing of removing the coating is a function of the application for which the coating is employed.

Film removal can be achieved by dissolution or dispersion of the resulting coating. This can be achieved by the application an aqueous solution onto the coating. In one embodiment, the temperature of the solution is in the range of about 15 degrees Centigrade to about 100 degrees Centigrade. In another embodiment, the temperature of the solution is from about 30 to about 80 degrees Centigrade. The application of the solution, or water, can be achieved by a simple rinse or spray onto the surface. Coating removal can also be achieved by use of a pressure washer, facilitating removal by additional mechanical forces. Coating removal can also be achieved by washing with water together with a cloth or sponge. Further, mild additives can utilized or mixed with the aqueous solution to help solubilize or disperse the film-forming or water-dispersible agents, including commonly used acids or bases, chelators or detergents. Alternatively, the film can be degraded, such as in a drain, by repeated washing of water and/or other components down the drain. The film can also be removed by peeling it off a surface, being abraded or brushed from the surface, or other mechanical mechanisms of removal.

Besides the intentional removal by an operator, removal also includes the removal by an automated or robotic system and the non-intentional removal by a liquid continuously or periodically contacting the coating over time, e.g. in a pipe or drain, or by continuous or periodical application of mechanical forces, such as wear.

Other Terms:

For clarity, terms used herein are to be understood as described herein or as such term would be understood by one of ordinary skill in the art of the invention. Additional, explanation of certain term used herein, are provided below:

Aqueous Solution:

An aqueous solution used for coating removal is any solution containing 60 to 100 wt-% water, the remaining components being dissolved components. Dissolved components can include but are not limited to solvents such as alcohols, solubilizing agents, surfactants, salts, chelators, acids and bases.

Durable:

Durable in this context relates to the dried coating matter remaining on the surface until its removal is purposely initiated or allowed to occur. Use conditions are the environmental conditions prevalent during the period the coating remains on the target surface for the application areas of this invention and can include inadvertent contact with water of a temperature below 40 degrees Centigrade.

Continuous:

Continuous, or substantially continuous, in this context refers to a coating that covers the target surface without uncovered areas, coating defects, such as craters and holes.

Homogeneous:

Homogeneous, or substantially homogenous, in this context refers to a coating with only negligible thickness variations across the coating surface. Coatings that are not homogeneous or not substantially homogenous will not provide even antimicrobial and removal properties across the whole surface the coating is applied to.

Residual Antimicrobial Efficacy:

The term 'residual antimicrobial efficacy' (or self-sanitizing properties) describes the property of coatings as described herein which remain active even after repeated challenges with microbes. According to this invention, at least a 3-log unit reduction is achieved by the methods herein. According to this invention at least a 3-log unit reduction is required after each inoculation over at least 2 inoculation cycles of at least $10^6$ cells per square inch. The test method used to determine residual antimicrobial efficacy is described in Example 16.

Contact Time for the Antimicrobial Coating:

Depending on the specific requirements for the antimicrobial formulations, the contact time would vary, as set out in Germicidal and Detergent Sanitizing Action of Disinfectants, Official Methods of Analysis of the Association of Official Analytical Chemists, paragraph 960.09 and applicable sections, 15th Edition, 1990 (EPA Guideline 91-2). If the intended application of the present invention is use as a sanitizer, then the composition should provide a 99.999% reduction (5-log order reduction) within 30 seconds at room temperature (25+/−2° C.) against several test organisms. On the other hand, if the intention is to use the invention as a disinfectant, then the composition should provide a 99.9% reduction (3-log order reduction) within 10 minutes. If the intended application is to be applied as a residual antimicrobial activity, then the present invention would be allowed to have greater than 10 minute contact time with microorganisms.

Physical Barrier:

A physical barrier is defined as the film formed from the present film forming composition. The resulting film seals the treated surface from contamination from the surrounding, such as soil, fat, dust, microorganisms etc. These contaminants will remain on the surface of the coating and will wash off at the time of removal of the coating.

All of the methods and compositions disclosed and claimed herein can be made and executed without undue experimentation in light of the present disclosure. While the methods and compositions of the present disclosure have been described in terms of various aspects of the invention and preferred embodiments, it will be apparent to those of skill in the art that variations can be applied to the compositions and methods and in the steps or in the sequence of steps of the method described herein without departing from the concept, spirit, and scope of the invention. More specifically, it will be apparent that certain agents, which are chemically related, can be substituted for the agents described herein while the same or similar results would be achieved. All such similar substitutes and modifications apparent to those skilled in the art are deemed to be within the spirit, scope, and concept of the invention as defined by the appended claims.

EXAMPLES

The present invention is further defined in the following Examples. It should be understood that these Examples, while indicating certain preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various uses and conditions.

Abbreviations and other Terms:

In the following examples, "degrees Centigrade" is abbreviated "° C.".

ATCC—American Type Culture Collection
BHI—brain heart infusion
BHT—butylated hydroxytoluene
CFU—colony forming unit
Conc.—concentration
cP—centipoise
DI—deionized
L—liter
LB—Luria Bertani broth
M—mole/liter
MW—molecular weight in grams/mole
NA—not applicable
ND—not determined
PBS—phosphate buffered saline solution (buffer)—10× stock solution contains (g/800 mL): NaCl (80); KCl (2.0); $NaH_2PO_4$(14.4); $KH_2PO_4$ (2.4) at pH 6.8
PEG—polyethylene glycol
PVOH—polyvinyl alcohol
QAC—quaternary ammonium compound
RAC—removable antimicrobial coating
RPM—revolutions per minute
SS316—stainless steel, type 316 (ASTM standard)
UHMWPE—ultra-high molecular-weight polyethylene
wt %—weight percent
ZOD—zone of diffusion All chemicals were obtained from Sigma-Aldrich (St. Louis, Mo., USA) unless stated otherwise. Laponite® was obtained from Rockwood Additives Ltd. (Widnes, UK). *Pseudomonas* F-Agar was obtained from Fisher Scientific (Pittsburgh, Pa., USA); yeast extract, Brain Heart Infusion (BHI), Tryptic Soy Agar, Tryptic Soy Broth, and Oxford Medium Base were from Difco products (Becton Dickenson, Franklin Lakes, N.J., USA); dextrose and magnesium sulfate heptahydrate were from JT Baker (Phillipsburg, N.J., USA); Elvanol® (71-30 and 52-22), polyurethane (RCP 31374), Zonyl® surfactants and titanium dioxide were from DuPont (Wilmington, Del., USA). Kollicoat®-IR was obtained from BASF (Ludwigshafen, Germany). Silwet®L-77 was obtained from GE Silicones (Wilton, Conn., USA). BYK® 425 was obtained from BYK Chemie (BYK-Chemie GmbH, Wesel, Germany). DowCorning® Q-5211 and Antifoam C were obtained from DowCorning® Silicones (Midland, Mich., USA). Silsurf® A012 was obtained from Siltech Corp. (Toronto, ON, Canada). Sil-co-sil® was obtained from U.S. Silica® Company (Berkeley Springs, W. Va., USA). Ticaxan, Carrageenan, and Guar 8/22 were supplied by TIC Gums (Belcamps, Md., USA). Alcogum® L1228, L15, L520 and L251 rheology additives were obtained from Alco Chemical® (Chattanooga, Tenn., USA) and were neutralized as specified by the supplier upon formulation after addition to antimicrobial compositions. Viskalex® HV100 and HV30 were obtained from Ciba® (Basel, Switzerland).

General Methods:

Test Methods for Antimicrobial Efficacy in Solutions:

Biocidal or antimicrobial efficacy in solutions can be determined by assays generally known in the art and as described in the following Examples.

Test Method for Antimicrobial and Antifungal Efficacy of Coatings by Zone-of-Diffusion Test:

To evaluate the antimicrobial and antifungal efficacy of antimicrobial coatings a zone-of diffusion (ZOD) test was employed as described below.

Stainless steel coupons (1 inch×3 inch) were dipped into RAC formulations and allowed to dry completely overnight. An overnight culture of *Staphylococcus aureus* ATCC 6358 was prepared by taking with a sterile inoculating loop a single colony from a refrigerated stock plate and inoculating into 25 mL of tryptic soy broth in a 250 mL sterile Erlenmeyer flask. The culture was incubated overnight at 30° C. while shaking at 150 RPM. Fungal spores (*Aspergillus niger* and *Penicillium expansium*) were prepared by growing stock plates (malt extract agar) for 2 weeks at 25° C., and harvesting spores by flooding plates with 15 mL of filter-sterilized saline solution (0.85% NaCl plus 0.05% Triton X-100). Plates were then scraped with a sterile plastic cell scraper, the liquid was pipetted off, vortexed and filtered through 3-4 layers of sterile cheesecloth. Spore suspension CFU was determined by plating serial dilutions onto malt extract agar plates. Coated coupons were placed on the surface of LB agar plates (center of plate) for 60 minutes, allowing soluble components of the coating to diffuse into the agar. A soft agar (0.7 wt-% agar in PBS buffer or water) was prepared, aliquoted into 5 mL portions in sterile plastic centrifuge tubes and held at 50° C. in a water bath until use. After 60 minutes, the coupons were removed by lifting straight up with sterile forceps, taking care not to slide the coupons across surface of agar. Any coating pieces that are left on the surface of the agar were also removed with sterile forceps. Each soft agar tube is inoculated with 100 μL of a 1:10 dilution of the overnight bacterial culture prepared above. The soft agar was inoculated with approximately $10^3$ spores/mL when fungal spores were used in the test. The agar was mixed gently by rocking tube and then agar was poured onto surface of LB agar plates which held coated coupons. Plates were swirled to completely cover surface with soft agar. The soft agar solidified almost immediately. Bacterial inoculated plates were incubated overnight at 35° C. and fungal inoculated plates were incubated at 25° C. for 2 days. All plates were photographed to record the zone of inhibition provided by the antimicrobial that diffused from the antimicrobial coating into the agar. The area of this zone of diffusion (ZOD) was analyzed by image analysis software (ImageJ, version 1.36b, National Institute of Health, USA) and normalized by the area of the coupons used. All agar diffusion studies had control coupons coated with a formulation lacking the antimicrobial agent.

Determination of rheological properties: The rheological properties of liquid antimicrobial formulations was assessed using a rheometer, running ascending and descending flow curves. The rheometer used was a Brookfield HADV-III+ (Brookfield Engineering, Middleboro, Mass., USA) with a couefte geometry, small sample adapter, spindle SC4-21 and sample chamber 13RP. The temperature was kept at 25° C. with a thermostat bath. Samples were loaded by pouring or scooping into the Brookfield sample holder. The program contained a pre-shear time of 5 min. at a pre-shear shear rate of 250 1/s, followed by a rest time of 10 min. Viscosity measurement were taken at: 0.1, 0.5, 5, 50, 100, 200, 100, 50, 5, 0.5, 0.1 RPM. The viscosity measurement interval was 2 min.

Example 1

Polyvinyl alcohol (PVOH) (DuPont Elvanol®, grade 71-30, MW approximately 94,000, degree of hydrolysis 99.0-99.8%; DuPont, Wilmington, Del., USA) was used as the film forming agent. PVOH stock solutions were prepared by mixing Elvanol®) grade 71-30 powder into deionized water of 90° C. to yield a 3 to 8 wt % solution. The mixture was stirred using a magnetic bar stirrer for approximately 20 minutes until the polyvinyl alcohol was completely dissolved. The mixture was allowed to cool to room temperature.

Blend base solutions were prepared by mixing the polyvinyl alcohol stock solutions with varying amounts of benzalkonium chloride (QAC) as active biocide, poly(ethylene glycol) (PEG) of MW-300 grams/mole as film plasticizer, polyoxyethylene sorbitan laurate surfactants as wetting agent(s), and butylated hydroxytoluene (BHT) as antioxidant. The QAC used was a mixture of mostly C12 and C14 analogues of alkylbenzyldimethyl-ammonium chloride (Sigma-Aldrich) but also contained small amounts of lower and higher analogues.

The blend base solution was then mixed with additional additives to yield the final spray formulation. These additives included cross-linkers such as ferric and ferrous chloride, rheology control modifiers such as synthetic layered silicate (Laponite®), and colorants and opacifying agents, such as food colorants and titanium dioxide. Liquid film-forming mixtures were prepared as outlined in Table 1. The mixtures are referenced in the subsequent examples by formulation number.

TABLE 1

Examples of film-forming antimicrobial compositions prepared using PVOH (Elvanol ® grade 71-30)

| | Formulation number | | | | | | | | | | | | | |
|---|---|---|---|---|---|---|---|---|---|---|---|---|---|---|
| | #2 | #10 | #14a | #16 | #17 | #18 | #19 | #20 | #21 | #22 | #23 | #24 | #25 | #26 |
| Deionized water | 95.9% | 96.1% | 95.0% | 95.2% | 90.9% | 95.1% | 96.6% | 96.5% | 96.1% | 96.4% | 96.3% | 95.9% | 94.4% | 94.5% |
| Elvanol ® 71-30 | 4.0% | 2.9% | 2.9% | 1.4% | 2.73% | 3.0% | 3.0% | 3.0% | 3.0% | 3.0% | 3.0% | 3.0% | 4.0% | 4.0% |
| PEG-300 | — | — | 0.29% | 0.51% | 1.00% | 0.21% | 0.21% | 0.21% | 0.21% | 0.21% | 0.21% | 0.21% | 0.28% | 0.28% |
| Tween ® 20 | — | — | 1.08% | — | 1.22% | 0.02% | 0.02% | 0.02% | 0.02% | 0.02% | 0.02% | 0.02% | 0.02% | 0.28% |
| Tween ® 60 | — | — | — | 0.5% | 2.2% | — | — | — | — | — | — | — | — | — |
| $FeCl_3 \cdot 6H_2O$ | — | — | 0.057% | — | — | 0.090% | — | — | — | — | — | — | — | — |
| $FeCl_2 \cdot 4H_2O$ | — | — | — | 0.48% | 0.95% | — | — | 0.10% | 0.50% | — | 0.10% | 0.50% | 0.12% | 0.12% |
| Benzalkonium chloride | 0.100% | 0.096% | 0.079% | 0.047% | 0.091% | 0.100% | 0.100% | 0.100% | 0.100% | 0.300% | 0.300% | 0.300% | 0.150% | — |
| Laponite ® clay | — | — | 0.560% | 1.40% | — | 1.40% | — | — | — | — | — | — | 1.00% | 1.00% |
| Kollicoat ® IR | — | 0.961% | — | 0.466% | 0.91% | — | — | — | — | — | — | — | — | — |
| BHT | — | — | — | — | — | 0.050% | 0.050% | 0.050% | 0.050% | 0.050% | 0.050% | 0.050% | 0.050% | 0.050% |
| Colorant | trace | — | trace | trace | trace | 0.060% | — | — | — | trace | trace | trace | — | — |
| Total | 100% | 100% | 100% | 100% | 100% | 100% | 100% | 100% | 100% | 100% | 100% | 100% | 100% | 100% |

Example 2

This example demonstrated that coatings are substantially continuous and homogeneous.

Films were prepared from the liquid mixtures outlined in Example 1. This was done by either spraying the liquids onto coupons (22 mm×60 mm) or by dipping coupons into the solutions. To spray the liquids they were filled into standard pump-action spray bottles and sprayed onto coupons. In most cases stainless steel was used as the coupon material. When spraying was used coupons were oriented vertically to model vertical food equipment surfaces to be treated with an antimicrobial formulation. For both dipping and spraying, coupons were then allowed to dry in vertical orientation at room temperature for at least 2 hours, typically overnight. The thickness of some films was measured using confocal laser-scanning microscopy after adding trace amounts of a fluorescent dye (rhodamine 123) to the film forming composition. A Zeiss LM 510 confocal microscope with Zeiss LSM-5 image analysis software (Carl Zeiss MicroImaging, Thornwood, N.Y., USA) was used.

Formulations with 4.0 wt-% PVOH were found to have a thickness of approx. 20 micrometers. Lower PVOH concentrations yielded thinner films. FIG. 2 shows cross sections of Formulation #2 through the depth of the film coating in two perpendicular planes. The high degree of uniformity in film thickness and absence of structural film defects (such as holes, cracks, craters, air inclusions etc.) can clearly be observed. High film uniformity is of high importance for protection functionality. Structural film defects or significant thickness variations could result in some areas remaining inefficiently protected from microbial contamination.

Different film textures were prepared depending on the formulations. Spraying of formulation #14a resulted in a rubbery and soft film after drying. In contrast, spraying of formulation #16 resulted in a very rigid and hard film after drying. Said textures can be utilized in accordance with operator need.

Dripping of the film-forming liquid from vertical surfaces after spraying could be prevented by addition of 0.5-1.5 wt % of colloidal synthetic layered silicate (Laponite® RD) as a thixotropic rheology control modifier.

Example 3

This example demonstrates that the coating solubility depends on cross linking agent concentration.

The formulation can be adjusted to allow easy removal of the film over a wide range of water temperatures. Film formulations can be developed to allow the film to be soluble in either cold or hot water temperatures. For example, films formed from Formulation #2 and #10 could easily be wiped off mechanically using a swab and could readily be dissolved after either a rinse of 20° C. or 98° C. water. Films formed from Formulation #14a could easily be wiped off mechanically and dissolved easily in 98° C. water but did not readily dissolve in 20° C. water. To achieve cold water stability a cross-linker had to be added to the mixture. Both Fe(II)-chloride and Fe(III)-chloride were suitable cross-linkers at concentrations between 0.1 and 1 wt % of the liquid formulation.

Example 4

Two plastic cover slips (type Thermanox® #174942, 22 mm×60 mm; Nalge Nunc International, Rochester, N.Y., USA) were dipped into a 4 wt % PVOH solution containing 1.0 g/L of benzalkonium chloride biocide. An additional two cover slips were dipped into a 4 wt % PVOH solution without benzalkonium chloride as control. The cover slips were placed into 50 mL centrifuge tubes and allowed to air-dry over night.

A culture of *Listeria* welshimeri (ATCC 35897) was prepared by growing a single cell colony in 25 mL BHI (37 g/L) in a 125 mL capacity shaker flask and incubated overnight at 30 C while shaking at 150 RPM. The cell concentration of this overnight culture was approximately $1\times10^9$ cells per mL. The culture was diluted 100-fold with modified Welshimer's medium (see Table 2 for medium composition) to provide a cell concentration of approximately $1\times10^7$ cells/mL. The coupons were placed in 50 mL centrifuge tubes and the cell suspension (10 mL) added to the tubes. Due to the high cell concentration the cell suspension was completely opaque in the 50 mL tube. Tubes were loosely covered with caps and incubated at 22° C. while shaking at 150 RPM.

After 24 hours, the liquid with the biocide QAC-containing coupon turned completely transparent to the human eye indicating considerable cell lysis. In contrast, the liquid with the coupon lacking QAC was still completely opaque indicating lack of any significant cell lysis.

TABLE 2

Formulation of Modified Weishimer growth medium used

| Ingredient | amount per liter | Supplier |
| --- | --- | --- |
| $KH_2PO_4$ | 6.56 g | JT Baker, Philipsburg, NJ, USA |
| $Na_2HPO_4*7H_2O$ | 30.96 g | Acros, Morris Plains, NJ, USA |
| $MgSO_4*7H_2O$ | 0.41 g | JT Baker, Philipsburg, NJ, USA |
| Ferric citrate | 0.088 g | Sigma-Aldrich, St. Louis, MO, USA |
| Glucose | 10 g | JT Baker, Philipsburg, NJ, USA |
| L-Leucine | 0.1 g | Sigma-Aldrich, St. Louis, MO, USA |
| L-Isoleucine | 0.1 g | Sigma-Aldrich, St. Louis, MO, USA |
| L-Valine | 0.1 g | Sigma-Aldrich, St. Louis, MO, USA |
| L-Methionine | 0.1 g | Sigma-Aldrich, St. Louis, MO, USA |
| L-Arginine | 0.1 g | Sigma-Aldrich, St. Louis, MO, USA |
| L-Cysteine | 0.1 g fresh | Sigma-Aldrich, St. Louis, MO, USA |
| L-Glutamine | 0.6 g fresh | Sigma-Aldrich, St. Louis, MO, USA |
| Riboflavin | 0.5 mg | Eastman, Rochester, NY, USA |
| Thiamine | 1.0 mg | Sigma-Aldrich, St. Louis, MO, USA |
| Biotin | 0.5 mg | Sigma-Aldrich, St. Louis, MO, USA |
| Thioctic acid | 0.005 mg | Sigma-Aldrich, St. Louis, MO, USA |

Example 5

One stainless steel coupon (format 22 mm×60 mm×1 mm) was coated with Formulation #22 by dipping and allowed to air-dry. A second coupon remained uncoated as control. The two coupons were placed into 50 mL centrifuge tubes.

A culture of L. welshimeri (strain DUP-1074) was prepared by growing a single cell colony in 25 mL of BHI as outlined above. The cell concentration of this overnight culture was approx. $1 \times 10^9$ cells per mL. The culture was diluted ×10,000 with modified Welshimer's medium to provide a cell concentration of approximately $1 \times 10^5$ cells/mL. This cell suspension (25 mL) was added to each coupon in 50 mL centrifuge tubes and the tubes were horizontally placed into an incubator-shaker and shaken at 25° C. while shaking at 150 RPM.

Samples (500 μL) were withdrawn from each tube after 10 and 240 minutes. Serial dilutions were made of each sample and 100 μL of each dilution was plated onto standard LB agar plates (Teknova, Inc., Hollister, Calif., USA) and incubated at 33° C. The number of CFU was counted after 24 hours. No significant decrease in cells (versus control) was observed in the sample taken after 10 minutes. However, the viable cell concentration reduced from $4.7 \times 10^4$ cells/mL to only 30 cells/mL after 240 minutes representing a significant 3.2 log reduction in the cell viability.

Example 6

Experiments were conducted to observe if surfaces sprayed with antimicrobial film coatings can delay the onset of biofilm formation. Coupons of stainless steel (SS316, 22 mm×60 mm×1 mm) were either sprayed with formulations #14a, #16 and #17 in vertical position or left untreated. The treated coupons were allowed to air-dry overnight in vertical position.

A culture of Pseudomonas fluorescens (ATCC 700830, Manassas, Va., USA) was prepared from a single colony grown overnight in 25 mL of standard M9 medium (see Table 3) at 30° C. while shaking at 150 RPM. The overnight culture was then diluted 100-fold with a solution of diluted LB medium (1.0 part LB diluted with 9 parts deionized water and filter sterilized). The diluted culture in the LB medium (10 mL) was added to each centrifuge tube. Tubes were loosely covered with caps and incubated while shaking at 150 RPM at 30° C. on. The medium was replaced each day by 10 mL fresh diluted LB medium.

Table 4 outlines biofilm control properties of selected antimicrobial PVOH films challenged with P. fluorescens ($\sim 1 \times 10^6$ cells/mL) and daily change of medium. The growth of biofilms was delayed with all formulations. With Formulation #14a no biofilm was observed after 2 days.

TABLE 3

M9 growth medium used

| Ingredient (sterile solutions) | amount per liter | Supplier |
| --- | --- | --- |
| 20% Glucose | 2.5 mL | JT Baker, Philipsburg, NJ, USA |
| 10% Bacto™ yeast extract | 0.2 mL | Difco, Sparks, MD, USA |
| 1.0 M $MgSO_4*7H_2O$ | 2 mL | JT Baker, Philipsburg, NJ, USA |
| 1.0 M $CaCl_2$ | 0.1 mL | Sigma-Aldrich, St. Louis, MO, USA |

TABLE 4

Biofilm control properties of selected antimicrobial PVOH films challenged with P. fluorescens ATCC 700830

| Film formulation | Result |
| --- | --- |
| Untreated control | Visible biofilm at interface after 24 hours. |
| Formulation #14a | No visual biofilm after 48 hours. |
| Formulation #16 | No visual biofilm after 24 hours. Slight biofilm starting at interface after 48 hours. |
| Formulation #17 | No visual biofilm after 24 hours. Slight biofilm starting at interface after 48 hours. |

Example 7

The release of QAC from sprayed PVOH films was demonstrated by release experiments. Films were sprayed on stainless steel coupons, air-dried, submerged into deionized water and samples were taken over time to determine the released QAC. The concentration of the released QAC was determined by an HPLC method adapted from the literature (R. C. Meyer, J. Pharm. Sci. 1980, 69, 1148-1150).

FIG. 3 shows the weight fraction of QAC released from the films sprayed with Formulations #19, #20 and #21 over time. These three formulations differed only in the amount of the cross-linker added to the formulation. The film thickness for the sprayed films was approximately 7.0 μm as determined by a micrometer gage. The total QAC available in the film was calculated from the concentration in the liquid formulation and the film volume. The semi-logarithmical graph shows the released fraction of QAC over time up to 7 days. A very fast initial release of QAC can be observed for all three film types. The addition of iron salt to the formulation increases the amount of QAC released from the film. Adjusting the amount of cross-linker in the liquid formulation provides a means of controlling the release profile over time, allowing a controlled and sustained release of the antimicrobial agent.

Example 8

An aqueous solution (25 wt %) of benzalkonium chloride (QAC) was added to a 10 wt % aqueous solution of polyvinyl pyrrolidone (PVP K-120 in water; International Specialty Products, Wayne, N.J., USA) solution. The final concentration of PVP was 5 wt % and the final concentration of benzalkonium chloride was 1 wt %. This PVP film-forming solution was used to treat coupons for prevention of biofilm formation.

An overnight culture of L. welshimeri was grown from a single colony in 25 mL TSB/YE medium (Tryptic Soy Broth plus 0.6 wt % yeast extract) in a shaker flask (30° C. with shaking at 150 RPM) to a density of $1 \times 10^9$ cells per mL. Sterile centrifuge tubes were uncapped in a biohood and each PVC coupon that had been thoroughly sprayed with 70 wt % ethanol was placed in a centrifuge tube. The caps were left off of the tubes to allow the coupons to air dry. For biofilm formation experiments, an overnight culture of L. welshimeri was diluted 1:100 in the modified Welshimer's medium (for example: for 20 tubes/coupons, 2 mL of overnight culture plus 200 mL of modified Welshimer's medium was required). A portion of this solution (10 mL) was added to each centrifuge tube. The tubes were covered loosely with caps and incubated at 22° C. on a shaker while shaking at 150 RPM. The medium was replaced every other day with fresh modified Welshimer's medium.

For the experiments summarized in Table 5, the L. welshimeri was grown on PVC (polyvinyl chloride) coupons (22 mm×60 mm; Lid for Flexible Plate PVC coupons, Becton Dickenson) for a specified time (see Table 5) to form a biofilm. When the biofilm was formed, the coupon was treated with the PVP film-forming solution by coating 100 µL of the PVP film-forming solution onto each side of the coupon. The PVP film was allowed to remain on the coupon for a specified treatment time. At the end of the treatment time, each coupon was gently rinsed with sterile PBS to remove loosely adhering cells, and cell viability of the biofilm was determined as described below. Each treatment was carried out in duplicates.

To determine cell viability, the biofilm was removed from the coupons by scraping the coupons with a sterile object (for example, plastic, metal or wood). Both sides of the coupon were scraped and the film was re-suspended in 10 mL of PBS buffer. The suspension was mixed by vortexing to homogenize the cell suspension. Serial dilutions (1:10 in PBS buffer) of the cell suspensions were prepared, and 100 µL aliquots were spread onto Petri plates containing either the LB or the Modified Oxford Agar. The plates were incubated at 30-37° C. overnight, and colonies were counted the following day.

TABLE 5

Bactericidal activity of coupons treated with PVP and QAC against Listeria weishimeri

| Sample | Biofilm age (hr) | Treatment time (hr) | log reduction (CFU/mL) |
| --- | --- | --- | --- |
| PVP/QAC | 16 | 3 | 7.7 |
| PVP/QAC | 16 | 16 | 7.7 |
| PVP/QAC | 48 | 3 | 7.5 |
| PVP/QAC | 48 | 16 | 7.5 |
| PVP/no QAC | 16 | 3 | 0.7 |
| PVP/no QAC | 16 | 16 | 2.2 |
| PVP/no QAC | 48 | 3 | 2.1 |
| PVP/no QAC | 48 | 17 | 1.5 |

Example 9

A film-forming solution of PVP K-120 and benzalkonium chloride was prepared such that the final concentration of PVP was 5 wt % and the final concentration of benzalkonium chloride was 0.01 wt %. This solution was used to treat biofilm coupons as described in Example 8.

The L. welshimeri biofilm was grown on PVC coupons as described in Example 8 for 2 days after which the biofilm coupon was treated with the PVP film-forming solution as described in Example 8. The PVP film-forming solution was allowed to remain in contact with the biofilm for three hours. At the end of the treatment time, the cell viability of the biofilm was determined as described in Example 8. Each treatment was carried out in duplicate. The PVP film with 0.01 wt % benzalkonium chloride yielded a 7.7 log reduction in CFU/mL.

Example 10

Polyvinyl alcohol (PVOH) (MW 100,000, >99% hydrolyzed, Sigma Aldrich) was dissolved in water. Sodium dichloroisocyanurate was added to this PVOH solution to achieve a final film-forming composition of 0.1 wt % sodium dichloroisocyanurate, 5 wt % PVOH, and the balance to 100% of DI water. This composition was used to coat a PVC coupon which was covered by a 2 day old Listeria welshimeri biofilm (prepared as described in Example 8). Cell viability was determined as described in Example 8 after three hours of contact time. The PVOH coating with sodium dichloroisocyanurate yielded a 7.3 log reduction in CFU per mL.

Example 11

Polyurethane dispersion was synthesized as described in US2005/0215663 paragraphs 212 through 217 (see also paragraphs 154 through 187 for abbreviations). The preparation yielded a 30 wt % aqueous dispersion of polyurethane.

The polyurethane dispersion was diluted to 10 wt % with ethanol. A polyurethane film-forming composition was prepared by adding aqueous benzalkonium chloride solution to the diluted polyurethane dispersion. The final film-forming composition was 5 wt % polyurethane, 0.5 wt % benzalkonium chloride, 25 wt % ethanol and the balance to 100 wt % of DI water. The coating was applied to the surface of PVC coupons as described in Example 8, and the coupons were air dried and placed in sterile centrifuge tubes.

An culture of Pseudomonas aeruginosa (ATCC 27853) was grown overnight from a single colony in 25 mL of M9 Medium in a shaker flask (30° C. while shaking at 150 RPM) to a density of $1 \times 10^9$ cells per mL. The culture was then diluted 1:100 in 0.1×LB medium (for example: for 20 tubes/coupons, 2 mL of overnight culture plus 200 mL of one-tenth strength LB medium was required). A portion of this solution (10 mL) was added to each centrifuge tube to partially immerse the coupon. The tubes were covered loosely with caps and incubated at 30° C. for 24 hours while shaking at 150 RPM.

At the end of the treatment time, each coupon was gently rinsed with sterile PBS to remove loosely adhering cells, and cell viability of the biofilm was determined. Each treatment was carried out in duplicates.

Cell viability was determined as described in Example 8, except that *Pseudomonas* F Agar was used in the Petri plates. An 8 log reduction in CFU/mL was observed in this treatment; in addition, no visible biofilm formation was observed on treated coupons while the uncoated coupon which had a visible biofilm formation.

Example 12

Two pipes (PVC-1120, J-M Manufacturing, Livingston, N.J., USA) were cut open lengthwise to yield to half pipes. The pipes were taped together again from the outside using standard Scotch® duct tape (3M, St. Paul, Minn., USA). Pipe geometry is given in Table 6. The pipes were coated with formulation #91 using a Wagner spray system (Wagner Power Painter, Model 0500179, Wagner Spray Tech Corp., Plymouth, Minn., USA) by aligning the spray nozzle of the system coaxially to one end of the horizontally oriented pipes and spraying for 10 seconds.

Formulation #91 had the following composition: Elvanol® grade 71-30 (5.0 wt %); benzalkonium chloride (0.63 wt %); Silwet L-77® (0.15 wt %); BYK®-425 (0.1 wt %); erythrosine B (0.05 wt %) and the balance to 100 wt % of DI water.

Coverage of the coating was observed visually which was easily achieved as the coating was colored and had a high contrast to the white background of the pipe. Complete coverage of the top and bottom half of the pipe was achieved up to a certain depth which are summarized in Table 6. Even the small gaps between the two half-pipes where completely covered with coating up to a certain depth into the pipe as presented in the table. This example illustrates that the invention can also be used to coat partly closed, concave or hard-to-reach surfaces such as pipes and drains.

TABLE 6

Pipe properties and penetration of coating formulation

| Pipe properties and coating results | Pipe #1 | Pipe #2 |
|---|---|---|
| Inner diameter (mm) | 51 | 71 |
| Wall thickness (mm) | 4 | 6 |
| Length (mm) | 800 | 700 |
| Material | PVC | PVC |
| Pipe orientation during spraying | horizontal | horizontal |
| Penetration length to yield complete coating on top half of pipe (mm) | 390 | 430 |
| Penetration length to yield complete coating on bottom half of pipe (mm) | 700 | 550 |
| Penetration length to yield complete coating in gaps between half-pipes (mm) | 700 | 320 |

Example 13

This example illustrates how rheology modifiers provide a removable antimicrobial coating composition with a shear thinning behavior. Such behavior enables easy (good sprayability), efficient (no drip) and effective (homogeneous antimicrobial activity) application of the composition to the surface. The example also illustrates that the antimicrobial efficacy can be fully retained after the addition of a rheology modifier.

The compositions used in this examples are based on a solution of PVOH (5 wt %) in water and a selection of additives. Addition order and formulation methods (mixing, scale etc.) vary for specific formulations.

Here we report the viscosity in centipoise (cP) at a shear rate of 5 and 190 s$^{-1}$. High viscosities mean less waste from dripping. The ratio of the two viscosities is a measure for the shear thinning effect. A higher ratio points towards better shear thinning and good sprayability.

The formulation itself was used to assess the antimicrobial activity of the composition containing the rheology modifier by means of the zone-of-diffusion (ZOD) test described earlier using *Staphylococcus aureus* ATCC 6358. It was found that the tested rheology modifiers were either neutral or contributing positively to the antimicrobial activity of the coating.

The composition in this example was obtained by adding benzalkonium chloride (0.6 wt %), Silwet® L-77 (0.15 wt %), BYK®425 (0.1 wt %) and erythrosine B (0.05 wt %) to a solution of PVOH (5 wt %, Elvanol® 71-30) in the balance to 100 wt % of DI water. In a second formulation step the rheology modifiers were added (see Table 7).

TABLE 7

Rheological properties of rheology modifiers in a composition containing 5 wt % PVOH in DI water and antimicrobial activity according to the ZOD method using *Staphylococcus aureus* ATCC 6358.

| Rheology modifier | Level (wt %) | Viscosity at 5 s$^{-1}$ (cP) | Viscosity at 190 s$^{-1}$ (cP) | Viscosity ratio | Antimicrobial activity (ZOD) |
|---|---|---|---|---|---|
| None | 0 | <50 | <50 | NA | + |
| Guar 8/22 | 2 | 520 | 337 | 1.5 | ND |
| Carrageenan | 2 | 2760 | 491 | 5.6 | ND |
| Alcogum L520 | 4 | 300 | 134 | 2.2 | + |
| Alcogum L251 | 2 | 140 | 126 | 1.1 | ND |
| Alcogum L251 | 4 | 560 | 371 | 1.5 | + |
| Viskalex HV100 | 1 | 240 | 127 | 1.9 | ND |

+ indicates that the area of the zone of diffusion (ZOD) was equal or larger than the area of coated coupon used in the experiment.
ND denoted "not determined".
NA denoted "not applicable".

Example 14

This example illustrates that rheology agents can be used to provide shear-thinning properties to the coating formulation based on polyvinyl alcohol grades of different degrees of hydrolysis. The example also illustrates that the degree of shear thinning (viscosity ratio) can be adjusted by varying the level of rheology modifier added to the formulation. The rheology agent used in this example is Alcogum® L251.

The composition in this example was prepared by loading water (total of all ingredients 100 wt %) into a flask with magnetic stir bar, followed by Silwet® L-77 (0.1 wt %), benzalkonium chloride (0.05 wt %), PEG (M-300) (0.2 wt %), Alcogum® L251 (various levels in Table 8), PVOH (5 wt %, Elvanol® 71-30 in water) and indigo carmine dye (0.03 wt %).

TABLE 8

Rheological properties of rheology modifiers in aqueous compositions containing 5 wt % PVOH (Elvanol ®)

| Elvanol grade | Alcogum L251 (wt %) | Viscosity at 5 s$^{-1}$ (cP) | Viscosity at 190 s$^{-1}$ (cP) | Viscosity ratio |
|---|---|---|---|---|
| 71-30 | 0 | 104 | 78 | 1.3 |
| 71-30 | 1 | 829 | 336 | 2.5 |
| 71-30 | 2 | 6567 | 570 | 12 |
| 52-22 | 0 | <50 | <50 | NA |
| 52-22 | 1 | 352 | 197 | 1.8 |
| 52-22 | 2 | 2839 | 549 | 5.2 |

NA denoted "not applicable".

Example 15

This example illustrates the use of coating formulations according to this invention to prevent fungi from growing on surfaces.

Fungal spores (*Aspergillus niger* and *Penicillium expansium*) were prepared by growing stock plates (malt extract agar) for 2 weeks at 25° C., and harvesting spores by flooding plates with 15 mL of filter-sterilized saline solution (0.85% NaCl plus 0.05% Triton® X-100). Plates were then scraped with a sterile plastic cell scraper and the liquid is pipetted off, vortexed and filtered through 3-4 layers of sterile cheesecloth. 400 microliters of the coating formulation was spread onto 1 inch×1 inch stainless steel coupons with a sterile pipet tip.

The coating formulation #109 of this example consisted of 5 wt % Elvanol® 71-30, 0.2 wt % PEG (M-300), 0.2 wt % benzalkonium chloride, 0.1 wt % Silwet®) L-77, 0.05 wt % BYK®425, 0.01 wt % erythrosine B and the balance to 100 wt % of DI water. The coating formulation #115 used for the negative control experiments was identical to formulation #109 except that no benzalkonium chloride was added.

The surface was completely covered and the coatings were allowed to dry completely (3-4 hours or overnight) in a vertical flow biohood. A 10 mL aliquot of the spore suspension was centrifuged and the supernatant was discarded. Spores were re-suspended in the same volume of Czapek Dox Broth. 100 microliters of this inoculum was added to each coupon and allowed to dry for 5 minutes. Coupons were placed with the coated side up on water agar plates and incubated at room temperature in a dessicator with the bottom filled with water for 2-4 weeks and observed daily for fungal growth.

Example 16

This example illustrates the use of coating formulations according to this invention to allow antimicrobial efficacy over extended periods of time. The example also demonstrates continued antimicrobial efficacy after multiple reinoculations of the antimicrobial coating with microorganisms. The example also demonstrates the residual antimicrobial efficacy of coatings formed from the formulation. The example also illustrates that the antimicrobial coating is efficacious against Gram-positive (*Staphylococcus aureus*) and Gram-negative (*Klebsiella pneumoniae*) organisms.

To test for effect of multiple bacterial contaminations on the efficacy of antimicrobial coatings the following method was used. Microorganisms tested included *Staphylococcus aureus* ATCC 6358 and *Klebsiella pneumoniae* ATCC 4352. An overnight culture of the selected microorganism was prepared by taking a single colony from a refrigerated stock plate by loop and inoculating 25 mL of tryptic soy broth or other liquid medium in a 250 mL sterile plastic Erlenmeyer flask. The flask was incubated overnight at 30° C. while shaking at 150 RPM. Then, 0.4 mL of coating formulation was spread onto a 1 inch×1 inch stainless steel (SS316) coupons with a sterile pipet tip. The entire surface was covered and the coating was allowed to dry completely (3-4 hours or overnight) in a vertical flow biohood. Besides the antimicrobial containing formulations, coupons were also coated with formulations lacking the antimicrobial as a control. The overnight culture was then diluted 1:10 with phosphate dilution buffer. Five percent sterile fetal bovine serum may be added to the culture at this time as an additional challenge to the coating. 10 microliters of this 1:10 dilution were used each time to contaminate the coupon surfaces by dotting on with a pipet tip in at least 20 locations and waiting for 5 minutes. Then, two coupons for each coating formulation and two control coupons were placed in sterile plastic 50 mL centrifuge tubes containing 20 mL of Letheen neutralization broth. The tubes were sonicated for 10 seconds and shaked for 10 minutes (200 RPM at 25° C.). These samples were then diluted serially and plated onto LB agar plates for colony forming unit (CFU) determination. Plates were incubated at 35° C. overnight and colonies were counted the following day. The remaining coupons were incubated at room temperature in a dessicator with the bottom filled with water. After one hour, the remaining coupons are all reinoculated with 10 microliters of diluted culture as above. After 5 minutes, two coupons for each

TABLE 9

Fungistatic activity of antimicrobial coating #109 and control experiments

| Fungal strain | Inoculum (spores/mL) | Coated with formulation | QAC conc. (ppm) | Fungal growth after week | | | |
|---|---|---|---|---|---|---|---|
| | | | | 1 | 2 | 3 | 4 |
| *Aspergillus niger* | 10$^6$ | #109 | 2000 | – | – | – | – |
| *Aspergillus niger* | 10$^6$ | #115 | 0 | +++ | +++ | +++ | +++ |
| *Aspergillus niger* | 10$^6$ | No coating | 0 | +++ | +++ | +++ | +++ |
| *P. expansium* | 10$^6$ | #109 | 2000 | – | – | – | – |
| *P. expansium* | 10$^6$ | #115 | 0 | +++ | +++ | +++ | +++ |
| *P. expansium* | 10$^6$ | No coating | 0 | ++++ | +++ | +++ | +++ |

– indicates that no fungal growth was observed.
+++ indicates excessive fungal growth.

formulation are removed and treated as above. The process is repeated after 2 and 3 hours after the first inoculation of the coupons.

The coating formulation #119 used in this example consisted of 5 wt % Elvanol® 71-30, 0.2 wt % PEG (MW-300), 0.05 wt % benzalkonium chloride, 0.1 wt % Silwet® L-77, 0.01 wt % indigo carmine dye and the balance to 100 wt % of DI water. Tables 10 and 11 show that no viable cells of the two organisms used were recovered for the coupons coated with formulation #119 whereas the more the $10^6$ cells were recovered from the coupons coated with the identical formulation lacking the QAC.

TABLE 10

Effect of multiple inoculations with *Staphylococcus aureus* (ATCC 6358) on the efficacy of coating formulation #119

| Sample | QAC conc. (ppm) | Time (min) | CFU |
|---|---|---|---|
| 1 | 500 | 5 | 0 |
| 2 | 0 | 5 | $1.3 \times 10^6$ |
| 3 | 500 | 60 | 0 |
| 4 | 0 | 60 | $1.4 \times 10^6$ |
| 5 | 500 | 120 | 0 |
| 6 | 0 | 120 | $1.3 \times 10^6$ |
| 7 | 500 | 180 | 0 |
| 8 | 0 | 180 | $1.5 \times 10^6$ |

TABLE 11

Effect of multiple inoculations with *Klebsiella Pneumoniae* (ATCC 4352) on the efficacy of coating formulation #119

| Sample | QAC conc. (ppm) | Time (min) | CFU |
|---|---|---|---|
| 1 | 500 | 5 | 0 |
| 2 | 0 | 5 | $6.2 \times 10^6$ |
| 3 | 500 | 60 | 0 |
| 4 | 0 | 60 | $5.4 \times 10^6$ |
| 5 | 500 | 120 | 0 |
| 6 | 0 | 120 | $5.6 \times 10^6$ |
| 7 | 500 | 180 | 0 |
| 8 | 0 | 180 | $5.7 \times 10^6$ |

Example 17

This example illustrates the use of surfactants to form a film after the formulation is applied to a surface.

In this example an organosilicone (Silwet®L-77) was used as the surfactant and the formulations consisted of 5 wt % polyvinyl alcohol (Elvanol® 52-22), 0.2 wt % PEG (MW-300), 0.05 wt % benzalkonium chloride with varying concentrations of Silwet®L-77 between 0 and 1 wt % (see Table 12) and a balance to 100 wt % of DI water.

The surface tensions of the samples were measured at 26.3° C. using a Kruess K 11 tensiometer (Kruess GmbH, Hamburg, Germany) using a wetted length of 40.2 mm.

A 100 μL droplet of each sample was pipetted onto clean test surfaces of stainless steel (SS316) and ultra-high-molecular weight polyethylene (UHMWPE). Both SS316 and UHMWPE are key materials of construction of industrial equipment, such as those used for food processing. Droplets were applied to the surface and allowed to spread for 5 minutes before digital photographs of the test surfaces were taken and the area covered by the droplets measured by image analysis (ImageJ Software, version 1.36b, National Institute of Health, USA). The area covered by the droplets was used as a measure of the spreading efficacy of each formulation. Table 12 reports the results for two surface materials and the formulations tested.

Addition of 0.001 wt % of the organosilicone to the SS316 formulation resulted in improvement of the spreading property of this formulation compared to the formulation without the added surfactant. The formulation with 0.001 wt % of the organosilicone demonstrated a surface tension of 35.9 mN/m which translated to a 16% improvement over the formulation without the addition.

A more pronounced increase of the spreading area was observed when the surface tension was lowered to 22.5 mN/m or below using an organosilicone concentration of at least 0.3 wt %. Under these conditions, the spreading area was increased by more than 160% for SS316 and by more than 220% for UHMWPE compared to the formulation without added surfactant.

TABLE 12

Effect of Silwet ® L-77 surfactant addition to antimicrobial coating formulations on surface tension and spreading ability on SS316 and UHMWPE surfaces.

| Surfactant conc. | Surface tension | Spreading area (mm$^2$) of a 100 μL droplet | |
|---|---|---|---|
| (wt %) | (mN/m) | on SS316 | on UHMWPE |
| None | 38.8 | 72 | 90 |
| 0.001 | 35.9 | 84 | 90 |
| 0.003 | 33.7 | 91 | 91 |
| 0.010 | 29.1 | 93 | 105 |
| 0.030 | 25.7 | 109 | 116 |
| 0.100 | 24.1 | 114 | 138 |
| 0.300 | 22.5 | 194 | 296 |
| 1.000 | 21.2 | 213 | 310 |

Example 18

This example illustrates the use of small gas bubbles in the antimicrobial coating as a temporary opacifying agent. For some of the intended uses of this invention it is not always desired to have a permanent color of the coating. For example, for the coating of walls a colored or opaque coating could be considered unaesthetic and a transparent antimicrobial coating may be preferred instead. Leaving out a permanent colorant or opacifying agent has the disadvantage that the operator applying the coating does not obtain feedback on what parts of the surface to be coated have already been covered. To overcome this problem, the following embodiment of this invention can be applied. At least one foaming agent can be added to create small gas bubbles in the film that is created on the target surface. The gas bubbles act as an opacifying agent and turn the freshly applied film white. To prevent the gas bubbles to get incorporated into the dry film, at least one antifoaming agent is also added to the formulation. The antifoaming agent aids the breakdown of the gas bubbles while the film is still wet to yield a transparent coating after drying.

The formulation #134 used in this example consisted of 7 wt % Elvanol® 52-22, 0.2 wt % PEG (MW-300), 0.05 wt % benzalkonium chloride, 0.2 wt % Silwet® L-77, and the balance to 100 wt % of DI water. The formulation #134a used in this example was identical to formulation #134 except that it contained 120 ppm active ingredient of Antifoam C emulsion in the formulation.

The surfactants benzalkonium chloride and Silwet®) L-77 caused both of the above formulations to foam and gas bubbles (>1,000,000 per square meter) were visible in the film obtained directly after spraying of the formulations on a surface using an high-volume/low-pressure (HVLP) spray gun (Devilbiss GTI spray gun; air cap #2000; 1.5 mm fluid tip; E.I. DuPont Company spray booth, Room 112, 377 Fairall Street, Ajax, ON, Canada.) The spray conditions were as follows: 2-3 coat application totaling 5-20 microns film at 5° C.-25° C., 30-60% relative humidity). Bubbles were counted visually using 4 inch×4 inch square and are reported as bubbles per square meter. The gas bubbles gave the films a white appearance after spraying. Many of the gas bubbles disappeared as the film dried. The remainder was approximately 15,000 bubbles/square meter for formulation #134 lacking the Antifoam C. For formulation #134a, however, only 100-500 very small bubbles per square meter were obtained after drying of the film (see Table 14).

TABLE 14

Gas bubbles in film immediately after spraying and in dried coating, respectively.

| Formulation | Immediately after spraying | | Dried coating | |
| --- | --- | --- | --- | --- |
| | Gas bubbles (number per m²) | Appearance | Gas bubbles (number per m²) | Appearance |
| #134 | >1,000,000 | White film | 15,000 (large) | Transparent coating with visible bubbles |
| #134a | >1,000,000 | White film | 100-500 (tiny) | Transparent coating |

Example 19

This example illustrates the impact of film thickness on antimicrobial properties. The antimicrobial efficacy was measured by the zone-of-diffusion (ZOD) method using *Staphylococcus aureus* ATCC 6358. The composition of coating formulation #134 is described in Example 18. Thicker films result in a larger zone-of diffusion and thus improved biocidal properties of the coating.

TABLE 14

Antimicrobial efficacy as a function of coating thickness for formulation #134. Antimicrobial efficacy was determined by zone of diffusion method using *Staphylococcus aureus* ATCC 6358.

| Coating thickness (micrometers) | Antimicrobial efficacy (ZOD) (in coupon areas) |
| --- | --- |
| 8 | 1.89 |
| 12 | 2.12 |
| 15 | 2.33 |

We claim:

1. An antimicrobial composition being removable by application of water thereto having a viscosity ratio between 15 and 12 wherein said viscosity ratio is the ratio of viscosity at a shear rate of 5 s-1 to the viscosity at a shear rate of 190 s$^{-1}$, the composition comprising:
   i) 1 to 30 wt. % of a water soluble or water-dispersible film-forming agent selected from polyvinyl alcohols, polyvinyl alcohol copolymers, polyvinyl pyrrolidones, polyacrylic add, acrylate copolymers, ionic hydrocarbon polymers, polyurethanes or combinations thereof;
   ii) at least 0.001 wt. % of an antimicrobial agent;
   iii) at least 50 wt. % of an inert solvent;
   iv) a surfactant that provides a surface tension of the composition below 40 mN/m; and
   v) a rheology agent capable of adjusting the viscosity ratio.

2. The composition of claim 1, wherein the surface tension of the composition is below 35 mN/m.

3. The composition of claim 1, wherein the surfactant is an organosilicone.

4. The composition of claim 1, comprising 0.01 wt. % to 0.2 wt. % of the surfactant.

5. The composition of claim 1, wherein the composition provides a reduction of microorganisms of at least 3-log when applied to a contaminated surface.

6. The composition of claim 1, wherein the composition further comprises one or more: plasticizer, cross-linking agent, colorant, solubilizing agent, rheology modifier, antioxidant pH adjuster, antifoaming agent, lubricant, processing aid, color fastness agent, performance enhancing agent, or enzyme.

7. The composition of claim 1, wherein the composition is removable from a surface by applying the water at a temperature of about 15° C. to about 100° c.

8. The composition of claim 1, wherein the water soluble or water-dispersible film-forming agent is a polyvinyl alcohol or a polyvinyl alcohol copolymer.

9. The composition of claim 8, comprising about 2% to about 15% by weight of the polyvinyl alcohol or the polyvinyl alcohol copolymer.

10. The composition of claim 1, wherein the inert solvent is water.

11. The composition of claim 1, further comprising about 0.001% to about 1% by weight of at least one surfactant.

12. A method for controlling microorganisms at a locus, the method comprising:
   (a) applying to the locus a liquid coating composition having a degree of shear thinning, the composition comprising:
      i) 1 to 30 wt. % of a water soluble or water-dispersible film-forming agent selected from polyvinyl alcohols, polyvinyl alcohol copolymers, polyvinyl pyrrolidones, polyacrylic acid, acrylate copolymers, ionic hydrocarbon polymers, polyurethanes, or combinations thereof;
      ii) at least 0.001 wt. % of an antimicrobial agent;
      iii) at least 50 wt. % of an inert solvent;
      iv) a surfactant that provides a surface tension of the composition below 40 mN/m;
      v) a rheology agent capable of adjusting the viscosity ratio;
   wherein the composition has a viscosity ratio between 1.5 and 50 in which the viscosity ratio is the ratio of viscosity at a shear rate of 5 s-1 to the viscosity at a shear rate of 190 s-1; and (b) removing the coating composition from the locus by applying water to the locus.

13. The method of claim 12, wherein the water is applied at a temperature of about 15° C. to about 100° C.

14. The method of claim 12, wherein the composition is applied in a thickness of about 0.3 to about 300 microns.

15. The method of claim 12, wherein the composition is applied in a thickness of about 1.0 to about 30 microns.

16. The method of claim 12, wherein the composition is applied by spraying, aerosolizing, or pouring.

17. The method of claim 12, wherein the composition provides a reduction of microorganisms of at least 3-log when applied to a contaminated food processing surface.

18. The method of claim 12, wherein the water is applied by spraying onto the locus.

19. The method of claim 12, wherein the water is applied by pressure washing.

* * * * *